(12) United States Patent
Dong et al.

(10) Patent No.: US 11,896,767 B2
(45) Date of Patent: Feb. 13, 2024

(54) MODEL-DRIVEN SYSTEM INTEGRATION IN MEDICAL VENTILATORS

(71) Applicant: Covidien LP, Mansfield, MA (US)

(72) Inventors: Nancy F. Dong, Carlsbad, CA (US); Gabriel Sanchez, Valley Center, CA (US); Kun Li, San Diego, CA (US)

(73) Assignee: Covidien LP, Mansfield, MA (US)

( * ) Notice: Subject to any disclaimer, the term of this patent is extended or adjusted under 35 U.S.C. 154(b) by 368 days.

(21) Appl. No.: 17/178,349

(22) Filed: Feb. 18, 2021

(65) Prior Publication Data
US 2021/0290883 A1    Sep. 23, 2021

Related U.S. Application Data

(60) Provisional application No. 62/992,257, filed on Mar. 20, 2020.

(51) Int. Cl.
*A61M 16/08* (2006.01)
*A61M 16/00* (2006.01)
(Continued)

(52) U.S. Cl.
CPC ........ *A61M 16/08* (2013.01); *A61M 16/0003* (2014.02); *A61M 16/024* (2017.08);
(Continued)

(58) Field of Classification Search
CPC .. A61M 16/0057–0087; A61M 16/024; A61M 16/026; A61M 16/202; A61M 16/205
See application file for complete search history.

(56) References Cited

U.S. PATENT DOCUMENTS

| | | |
|---|---|---|
| 3,444,857 A | 5/1969 | Godel |
| 3,481,333 A | 12/1969 | Garrison |

(Continued)

FOREIGN PATENT DOCUMENTS

| | | |
|---|---|---|
| EP | 2844323 | 3/2015 |
| WO | 2007/102866 | 9/2007 |

(Continued)

OTHER PUBLICATIONS

International Search Report for International Application No. PCT/US2021/023170 dated Jul. 6, 2021 (4 pages).

(Continued)

*Primary Examiner* — Kendra D Carter
*Assistant Examiner* — Mautin I Ashimiu

(57) ABSTRACT

Systems and methods for model-driven system integration on a ventilator comprise a modeled exhalation flow. Ventilator flow sensors contain components that are easily damaged or impacted and have high rates of failure. Knowledge failure frequency and type may help determine when to replace, clean, or calibrate a flow sensor. A modeled exhalation flow may be trained for a ventilator. Additionally, the modeled exhalation flow may be compared to a flow sensor flow to determine a specific failure. Additionally or alternatively, the modeled exhalation flow may supplement, weight, or replace a faulty flow sensor measurement. These systems and methods may assist in identifying an inaccurate flow sensor measurement and/or providing a more accurate modeled flow estimate, thus increasing accuracy in patient-ventilator interactions.

13 Claims, 12 Drawing Sheets

(51) Int. Cl.
*A61M 16/20* (2006.01)
*G16H 20/40* (2018.01)
*G16H 40/63* (2018.01)
*G16H 40/40* (2018.01)

(52) U.S. Cl.
CPC ..... *A61M 16/205* (2014.02); *A61M 2016/003* (2013.01); *A61M 2016/0027* (2013.01); *A61M 2205/3368* (2013.01)

(56) References Cited

U.S. PATENT DOCUMENTS

| | | |
|---|---|---|
| 3,485,243 A | 12/1969 | Bird et al. |
| 3,688,794 A | 9/1972 | Bird et al. |
| 4,241,756 A | 12/1980 | Bennett et al. |
| 4,527,557 A | 7/1985 | DeVries et al. |
| 4,608,976 A | 9/1986 | Suchy |
| 4,699,137 A | 10/1987 | Schroeder |
| RE32,553 E | 12/1987 | Bennett et al. |
| 4,712,580 A | 12/1987 | Gilman et al. |
| 4,727,871 A | 3/1988 | Smargiassi et al. |
| 4,747,403 A | 5/1988 | Gluck et al. |
| 4,957,107 A | 9/1990 | Sipin |
| 4,991,576 A | 2/1991 | Henkin et al. |
| 4,993,269 A | 2/1991 | Guillaume et al. |
| 5,000,173 A | 3/1991 | Zalkin et al. |
| 5,020,532 A | 6/1991 | Mahoney et al. |
| 5,072,729 A | 12/1991 | DeVries |
| 5,109,838 A | 5/1992 | Elam |
| 5,127,400 A | 7/1992 | DeVries et al. |
| 5,134,995 A | 8/1992 | Gruenke et al. |
| 5,161,525 A | 11/1992 | Kimm et al. |
| 5,168,868 A | 12/1992 | Hicks |
| 5,178,155 A | 1/1993 | Mault |
| 5,237,987 A | 8/1993 | Anderson et al. |
| 5,255,675 A | 10/1993 | Kolobow |
| 5,259,373 A | 11/1993 | Gruenke et al. |
| 5,261,397 A | 11/1993 | Grunstein |
| 5,269,293 A | 12/1993 | Loser et al. |
| 5,277,175 A | 1/1994 | Riggs et al. |
| 5,299,568 A | 4/1994 | Forare et al. |
| 5,301,667 A | 4/1994 | McGrail et al. |
| 5,303,699 A | 4/1994 | Bonassa et al. |
| 5,309,901 A | 5/1994 | Beaussant |
| 5,331,995 A | 7/1994 | Westfall et al. |
| 5,339,807 A | 8/1994 | Carter |
| 5,343,858 A | 9/1994 | Winefordner et al. |
| 5,353,788 A | 10/1994 | Miles |
| 5,360,000 A | 11/1994 | Carter |
| 5,368,021 A | 11/1994 | Beard et al. |
| 5,383,449 A | 1/1995 | Forare et al. |
| 5,390,666 A | 2/1995 | Kimm et al. |
| 5,398,677 A | 3/1995 | Smith |
| 5,452,714 A | 9/1995 | Anderson et al. |
| 5,467,766 A | 11/1995 | Ansite et al. |
| 5,484,270 A | 1/1996 | Adahan |
| 5,494,028 A | 2/1996 | DeVries et al. |
| 5,497,767 A | 3/1996 | Olsson et al. |
| 5,503,140 A | 4/1996 | Winefordner et al. |
| 5,517,983 A | 5/1996 | Deighan et al. |
| 5,524,615 A | 6/1996 | Power |
| 5,540,220 A | 7/1996 | Gropper et al. |
| 5,542,416 A | 8/1996 | Chalvignac |
| 5,546,935 A | 8/1996 | Champeau |
| 5,549,106 A | 8/1996 | Gruenke et al. |
| 5,568,910 A | 10/1996 | Koehler et al. |
| 5,575,283 A | 11/1996 | Sjoestrand |
| 5,606,968 A | 3/1997 | Mang |
| 5,617,847 A | 4/1997 | Howe |
| 5,630,411 A | 5/1997 | Holscher |
| 5,632,270 A | 5/1997 | O'Mahony et al. |
| 5,657,750 A | 8/1997 | Colman et al. |
| 5,660,171 A | 8/1997 | Kimm et al. |
| 5,662,099 A | 9/1997 | Tobia et al. |
| 5,664,562 A | 9/1997 | Bourdon |
| 5,678,537 A | 10/1997 | Bathe et al. |
| 5,683,232 A | 11/1997 | Adahan |
| 5,692,497 A | 12/1997 | Schnitzer et al. |
| 5,697,363 A | 12/1997 | Hart |
| 5,701,883 A | 12/1997 | Hete et al. |
| 5,701,889 A | 12/1997 | Danon |
| 5,771,884 A | 6/1998 | Yarnall et al. |
| 5,794,614 A | 8/1998 | Gruenke et al. |
| 5,797,393 A | 8/1998 | Kohl |
| 5,803,064 A | 9/1998 | Phelps et al. |
| 5,813,399 A | 9/1998 | Isaza et al. |
| 5,823,179 A | 10/1998 | Grychowski et al. |
| 5,826,575 A | 10/1998 | Lall |
| 5,845,636 A | 12/1998 | Gruenke et al. |
| 5,857,458 A | 1/1999 | Tham et al. |
| 5,868,133 A | 2/1999 | DeVries et al. |
| 5,875,783 A | 3/1999 | Kullik |
| 5,876,352 A | 3/1999 | Weismann |
| 5,881,717 A | 3/1999 | Isaza |
| 5,881,722 A | 3/1999 | DeVries et al. |
| 5,915,381 A | 6/1999 | Nord |
| 5,918,597 A | 7/1999 | Jones et al. |
| 5,937,856 A | 8/1999 | Jonasson et al. |
| 5,941,846 A | 8/1999 | Duffy et al. |
| 5,957,130 A | 9/1999 | Krahbichler et al. |
| 6,041,777 A | 3/2000 | Faithfull et al. |
| 6,041,780 A | 3/2000 | Richard et al. |
| 6,073,630 A | 6/2000 | Adahan |
| 6,095,139 A | 8/2000 | Psaros |
| 6,102,038 A | 8/2000 | DeVries |
| 6,116,242 A | 9/2000 | Frye et al. |
| 6,119,686 A | 9/2000 | Somerson et al. |
| 6,123,074 A | 9/2000 | Hete et al. |
| 6,131,571 A | 10/2000 | Lampotang et al. |
| 6,135,967 A | 10/2000 | Fiorenza et al. |
| 6,148,814 A | 11/2000 | Clemmer et al. |
| 6,152,132 A | 11/2000 | Psaros |
| 6,152,135 A | 11/2000 | DeVries et al. |
| 6,158,432 A | 12/2000 | Biondi et al. |
| 6,176,234 B1 | 1/2001 | Salter et al. |
| 6,192,885 B1 | 2/2001 | Jalde |
| 6,217,524 B1 | 4/2001 | Orr et al. |
| 6,287,264 B1 | 9/2001 | Hoffman |
| 6,295,330 B1 | 9/2001 | Skog et al. |
| 6,295,985 B1 | 10/2001 | Kock et al. |
| 6,306,098 B1 | 10/2001 | Orr et al. |
| 6,308,706 B1 | 10/2001 | Lammers et al. |
| 6,309,360 B1 | 10/2001 | Mault |
| 6,349,922 B1 | 2/2002 | Rydin |
| 6,371,113 B1 | 4/2002 | Tobia et al. |
| 6,412,483 B1 | 7/2002 | Jones et al. |
| 6,415,788 B1 | 7/2002 | Clawson et al. |
| 6,419,634 B1 | 7/2002 | Gaston, IV et al. |
| 6,457,472 B1 | 10/2002 | Schwartz et al. |
| 6,467,477 B1 | 10/2002 | Frank et al. |
| 6,523,537 B1 | 2/2003 | Mas Marfany |
| 6,523,538 B1 | 2/2003 | Wikefeldt |
| 6,526,970 B2 | 3/2003 | DeVries et al. |
| 6,543,449 B1 | 4/2003 | Woodring et al. |
| 6,550,479 B1 | 4/2003 | Duxbury |
| 6,557,553 B1 | 5/2003 | Borrello |
| 6,557,554 B1 | 5/2003 | Sugiura |
| 6,564,798 B1 | 5/2003 | Jalde |
| 6,572,561 B2 | 6/2003 | Mault |
| 6,575,164 B1 | 6/2003 | Jaffe et al. |
| 6,575,165 B1 | 6/2003 | Cook et al. |
| 6,575,918 B2 | 6/2003 | Kline |
| 6,584,973 B1 | 7/2003 | Biondi et al. |
| 6,606,994 B1 | 8/2003 | Clark |
| 6,616,615 B2 | 9/2003 | Mault |
| 6,619,289 B1 | 9/2003 | Mashak |
| 6,622,725 B1 | 9/2003 | Fisher et al. |
| 6,622,726 B1 | 9/2003 | Du |
| 6,629,934 B2 | 10/2003 | Mault et al. |
| 6,631,716 B1 | 10/2003 | Robinson et al. |
| 6,668,824 B1 | 12/2003 | Isaza et al. |
| 6,722,359 B2 | 4/2004 | Chalvignac |
| 6,723,055 B2 | 4/2004 | Hoffman |
| 6,729,331 B2 | 5/2004 | Kay |

(56) References Cited

U.S. PATENT DOCUMENTS

| | | |
|---|---|---|
| 6,739,334 B2 | 5/2004 | Valeij |
| 6,763,829 B2 | 7/2004 | Jaffe et al. |
| 6,772,762 B2 | 8/2004 | Piesinger |
| 6,805,121 B1 | 10/2004 | Flood et al. |
| 6,837,242 B2 | 1/2005 | Younes |
| 6,866,040 B1 | 3/2005 | Bourdon |
| 6,877,511 B2 | 4/2005 | DeVries et al. |
| 6,886,558 B2 | 5/2005 | Tanaka |
| 6,896,713 B1 | 5/2005 | Eckerbom et al. |
| 6,938,619 B1 | 9/2005 | Hickle |
| 6,968,840 B2 | 11/2005 | Smith et al. |
| 6,981,947 B2 | 1/2006 | Melker |
| 7,032,589 B2 | 4/2006 | Kerechanin, II et al. |
| 7,040,315 B1 | 5/2006 | Strömberg |
| 7,040,321 B2 | 5/2006 | Göbel |
| 7,043,979 B2 | 5/2006 | Smith et al. |
| 7,066,175 B2 | 6/2006 | Hamilton et al. |
| 7,066,177 B2 | 6/2006 | Pittaway et al. |
| RE39,225 E | 8/2006 | Isaza et al. |
| 7,094,206 B2 | 8/2006 | Hoffman |
| 7,118,537 B2 | 10/2006 | Baddour |
| 7,121,277 B2 | 10/2006 | Ström |
| 7,152,604 B2 | 12/2006 | Hickle et al. |
| 7,168,597 B1 | 1/2007 | Jones et al. |
| 7,195,013 B2 | 3/2007 | Lurie |
| 7,210,478 B2 | 5/2007 | Banner et al. |
| 7,222,623 B2 | 5/2007 | DeVries et al. |
| 7,241,269 B2 | 7/2007 | McCawley et al. |
| 7,275,540 B2 | 10/2007 | Bolam et al. |
| 7,291,115 B2 | 11/2007 | Cardona Burrul |
| 7,302,949 B2 | 12/2007 | Pelerossi et al. |
| 7,320,321 B2 | 1/2008 | Pranger et al. |
| 7,347,825 B2 | 3/2008 | Vaughan et al. |
| 7,392,806 B2 | 7/2008 | Yuen et al. |
| 7,475,685 B2 | 1/2009 | Dietz et al. |
| 7,484,508 B2 | 2/2009 | Younes |
| 7,487,778 B2 | 2/2009 | Freitag |
| 7,500,483 B2 | 3/2009 | Colman et al. |
| 7,509,957 B2 | 3/2009 | Duquette et al. |
| 7,525,663 B2 | 4/2009 | Kwok et al. |
| 7,533,670 B1 | 5/2009 | Freitag et al. |
| 7,547,285 B2 | 6/2009 | Kline |
| 7,556,038 B2 | 7/2009 | Kirby et al. |
| 7,556,042 B2 | 7/2009 | West et al. |
| 7,562,657 B2 | 7/2009 | Blanch et al. |
| 7,588,033 B2 | 9/2009 | Wondka |
| 7,610,914 B2 | 11/2009 | Bolam et al. |
| 7,617,824 B2 | 11/2009 | Doyle |
| 7,621,271 B2 | 11/2009 | Brugnoli |
| 7,634,998 B1 | 12/2009 | Fenley |
| 7,682,312 B2 | 3/2010 | Lurie |
| 7,686,019 B2 | 3/2010 | Weiss |
| 7,699,788 B2 | 4/2010 | Kuck et al. |
| 7,717,113 B2 | 5/2010 | Andrieux |
| 7,721,735 B2 | 5/2010 | Hamilton et al. |
| 7,721,736 B2 | 5/2010 | Urias et al. |
| 7,740,591 B1 | 6/2010 | Starr et al. |
| 7,753,052 B2 | 7/2010 | Tanaka |
| 7,779,840 B2 | 8/2010 | Acker et al. |
| 7,810,497 B2 | 10/2010 | Pittman et al. |
| 7,814,908 B2 | 10/2010 | Psaros |
| 7,819,815 B2 | 10/2010 | Younes |
| 7,828,741 B2 | 11/2010 | Kline et al. |
| 7,846,739 B2 | 12/2010 | von Bahr et al. |
| 7,849,854 B2 | 12/2010 | DeVries et al. |
| 7,861,716 B2 | 1/2011 | Borrello |
| 7,870,857 B2 | 1/2011 | Dhuper et al. |
| 7,883,471 B2 | 2/2011 | Aljuri et al. |
| 7,885,771 B2 | 2/2011 | Roecker et al. |
| 7,900,626 B2 | 3/2011 | Daly |
| 7,913,690 B2 | 3/2011 | Fisher et al. |
| 8,322,339 B2 | 12/2012 | Gottlib |
| 8,434,479 B2 | 5/2013 | Jafari |
| 9,027,552 B2 | 5/2015 | Angelico |
| 9,492,629 B2 | 11/2016 | Sanchez |
| 9,925,346 B2 | 3/2018 | Dong |
| 2002/0026941 A1 | 3/2002 | Biondi et al. |
| 2002/0138213 A1 | 9/2002 | Mault |
| 2003/0062045 A1 | 4/2003 | Woodring et al. |
| 2004/0138577 A1 | 7/2004 | Kline |
| 2004/0261793 A1 | 12/2004 | Stromberg et al. |
| 2005/0098177 A1 | 5/2005 | Haj-Yahya et al. |
| 2005/0139211 A1 | 6/2005 | Alston et al. |
| 2005/0150494 A1 | 7/2005 | DeVries et al. |
| 2005/0217671 A1 | 10/2005 | Fisher et al. |
| 2006/0032499 A1 | 2/2006 | Halsnes |
| 2006/0129054 A1 | 6/2006 | Orr et al. |
| 2006/0130839 A1 | 6/2006 | Bassovitch |
| 2006/0201507 A1 | 9/2006 | Breen |
| 2006/0249148 A1 | 11/2006 | Younes |
| 2006/0249153 A1 | 11/2006 | DeVries et al. |
| 2007/0000494 A1 | 1/2007 | Banner et al. |
| 2007/0028921 A1 | 2/2007 | Banner et al. |
| 2007/0062531 A1 | 3/2007 | Fisher et al. |
| 2007/0068530 A1 | 3/2007 | Pacey |
| 2007/0073183 A1 | 3/2007 | Kline |
| 2007/0095347 A1 | 5/2007 | Lampotang et al. |
| 2007/0113854 A1 | 5/2007 | Mcauliffe |
| 2007/0125377 A1 | 6/2007 | Heinonen et al. |
| 2007/0144521 A1 | 6/2007 | DeVries et al. |
| 2007/0144523 A1 | 6/2007 | Bolam et al. |
| 2007/0157930 A1 | 7/2007 | Soliman et al. |
| 2007/0157931 A1 | 7/2007 | Parker et al. |
| 2007/0163579 A1 | 7/2007 | Li et al. |
| 2007/0232952 A1 | 10/2007 | Baddour |
| 2007/0255160 A1 | 11/2007 | Daly |
| 2008/0045825 A1 | 2/2008 | Melker et al. |
| 2008/0053438 A1 | 3/2008 | DeVries et al. |
| 2008/0060646 A1 | 3/2008 | Isaza |
| 2008/0060656 A1 | 3/2008 | Isaza |
| 2008/0135044 A1 | 6/2008 | Freitag et al. |
| 2008/0183094 A1 | 7/2008 | Schonfuss et al. |
| 2008/0196720 A1 | 8/2008 | Kollmeyer et al. |
| 2008/0202517 A1 | 8/2008 | Mitton et al. |
| 2008/0202518 A1 | 8/2008 | Mitton et al. |
| 2008/0214947 A1 | 9/2008 | Hunt et al. |
| 2008/0230062 A1 | 9/2008 | Tham |
| 2008/0257349 A1 | 10/2008 | Hedner et al. |
| 2008/0276939 A1 | 11/2008 | Tiedje |
| 2009/0000621 A1 | 1/2009 | Haggblom et al. |
| 2009/0007914 A1 | 1/2009 | Bateman |
| 2009/0050153 A1 | 2/2009 | Brunner |
| 2009/0056708 A1 | 3/2009 | Stenzler et al. |
| 2009/0056719 A1 | 3/2009 | Newman, Jr. |
| 2009/0071478 A1 | 3/2009 | Kalfon |
| 2009/0078251 A1 | 3/2009 | Zucchi et al. |
| 2009/0084381 A1 | 4/2009 | DeVries et al. |
| 2009/0090359 A1 | 4/2009 | Daviet et al. |
| 2009/0114223 A1 | 5/2009 | Bonassa |
| 2009/0133695 A1 | 5/2009 | Rao et al. |
| 2009/0137919 A1 | 5/2009 | Bar-Lavie et al. |
| 2009/0188502 A1 | 7/2009 | Tiedje |
| 2009/0217923 A1 | 9/2009 | Boehm et al. |
| 2009/0221926 A1 | 9/2009 | Younes |
| 2009/0229612 A1 | 9/2009 | Levi et al. |
| 2009/0235935 A1 | 9/2009 | Pacey |
| 2009/0241948 A1 | 10/2009 | Clancy et al. |
| 2009/0241951 A1 | 10/2009 | Jafari et al. |
| 2009/0241955 A1 | 10/2009 | Jafari et al. |
| 2009/0241964 A1 | 10/2009 | Aljuri et al. |
| 2009/0247891 A1 | 10/2009 | Wood |
| 2009/0250054 A1 | 10/2009 | Loncar et al. |
| 2009/0250059 A1 | 10/2009 | Allum et al. |
| 2009/0255533 A1 | 10/2009 | Freitag et al. |
| 2009/0260625 A1 | 10/2009 | Wondka |
| 2009/0263279 A1 | 10/2009 | Kline et al. |
| 2009/0270752 A1 | 10/2009 | Coifman |
| 2009/0277448 A1 | 11/2009 | Ahlmén et al. |
| 2009/0293877 A1 | 12/2009 | Blanch et al. |
| 2009/0299430 A1 | 12/2009 | Davies et al. |
| 2009/0301486 A1 | 12/2009 | Masic |
| 2010/0012126 A1 | 1/2010 | Gandini |
| 2010/0031961 A1 | 2/2010 | Schmidt |
| 2010/0051029 A1 | 3/2010 | Jafari et al. |

(56) References Cited

U.S. PATENT DOCUMENTS

| | | |
|---|---|---|
| 2010/0059058 A1 | 3/2010 | Kuo |
| 2010/0071696 A1 | 3/2010 | Jafari |
| 2010/0099999 A1 | 4/2010 | Hemnes et al. |
| 2010/0101577 A1 | 4/2010 | Kaestle et al. |
| 2010/0106037 A1 | 4/2010 | Kacmarek et al. |
| 2010/0125227 A1 | 5/2010 | Bird |
| 2010/0137733 A1 | 6/2010 | Wang et al. |
| 2010/0139660 A1 | 6/2010 | Adahan |
| 2010/0147302 A1 | 6/2010 | Selvarajan et al. |
| 2010/0170512 A1 | 7/2010 | Kuypers et al. |
| 2010/0175695 A1 | 7/2010 | Jamison |
| 2010/0179392 A1 | 7/2010 | Chang et al. |
| 2010/0180897 A1 | 7/2010 | Malgouyres |
| 2010/0185112 A1 | 7/2010 | Van Kesteren et al. |
| 2010/0186744 A1 | 7/2010 | Andrieux |
| 2010/0198095 A1 | 8/2010 | Isler |
| 2010/0218765 A1 | 9/2010 | Jafari et al. |
| 2010/0218767 A1 | 9/2010 | Jafari et al. |
| 2010/0222692 A1 | 9/2010 | McCawley et al. |
| 2010/0236553 A1 | 9/2010 | Jafari et al. |
| 2010/0241019 A1 | 9/2010 | Varga et al. |
| 2010/0249584 A1 | 9/2010 | Albertelli |
| 2010/0252042 A1 | 10/2010 | Kapust et al. |
| 2010/0268106 A1 | 10/2010 | Johnson et al. |
| 2010/0268131 A1 | 10/2010 | Efthimiou |
| 2010/0269834 A1 | 10/2010 | Freitag et al. |
| 2010/0282258 A1 | 11/2010 | Tailor et al. |
| 2010/0286544 A1 | 11/2010 | Tanaka et al. |
| 2010/0292601 A1 | 11/2010 | Dompeling et al. |
| 2010/0324437 A1 | 12/2010 | Freeman et al. |
| 2010/0324439 A1 | 12/2010 | Davenport |
| 2011/0004108 A1 | 1/2011 | Peyton |
| 2011/0009762 A1 | 1/2011 | Eichler et al. |
| 2011/0023879 A1 | 2/2011 | Vandine et al. |
| 2011/0041850 A1 | 2/2011 | Vandine et al. |
| 2011/0066060 A1 | 3/2011 | von Bahr et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2012/0216809 A1 | 8/2012 | Milne |
| 2013/0152934 A1 | 6/2013 | Mulqueeny et al. |
| 2014/0261409 A1 | 9/2014 | Dong et al. |
| 2016/0206837 A1 | 7/2016 | Dong et al. |
| 2017/0367617 A1 | 12/2017 | Albanese et al. |

FOREIGN PATENT DOCUMENTS

| | | | | |
|---|---|---|---|---|
| WO | WO-2016118628 A1 | * | 7/2016 | ............ A61M 16/00 |
| WO | WO-2021016662 A1 | * | 2/2021 | ........ A61M 16/0003 |

OTHER PUBLICATIONS

International Written Opinion for International Application No. PCT/US2021/023170 dated Jul. 6, 2021 (8 pages).

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Puritan Bennett 980 Series Ventilator Operator's Manual, Covidien, Jan. 29, 2014, Part. No. 10077893 A Jan. 2014, 506 pages.

* cited by examiner

MODEL-DRIVEN SYSTEM INTEGRATION IN MEDICAL VENTILATORS

CROSS-REFERENCE TO RELATED APPLICATIONS

This application claims the benefit of U.S. Provisional Application No. 62/992,257, filed Mar. 20, 2020, the complete disclosure of which is hereby incorporated herein by reference in its entirety.

INTRODUCTION

Medical ventilator systems have long been used to provide ventilatory and supplemental oxygen support to patients. These ventilators typically comprise a connection for pressurized gas (air, oxygen) that is delivered to the patient through a conduit or tubing. As each patient may require a different ventilation strategy, and modern ventilators can be customized for the particular needs of an individual patient. For example, several different ventilator modes or settings have been created to provide better ventilation for patients in different scenarios, such as mandatory ventilation modes, spontaneous ventilation modes, and assist-control ventilation modes. Ventilators monitor a variety of patient parameters and are well equipped to provide reports and other information regarding a patient's condition.

It is with respect to this general technical environment that aspects of the present technology disclosed herein have been contemplated. Furthermore, although a general environment is discussed, it should be understood that the examples described herein should not be limited to the general environment identified herein.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

Among other things, aspects of the present disclosure include systems and methods for model-driven system integration for estimating an exhalation flow. More specifically, this disclosure describes systems and methods for determining a failure of a flow sensor, e.g., an exhalation flow sensor. This may help determine when to replace, clean, or calibrate a flow sensor. A modeled flow may be trained for a ventilator, e.g., a modeled exhalation flow. Additionally, a modeled exhalation flow may be compared to an exhalation flow measured by an actual flow sensor, to determine a specific failure. Additionally or alternatively, the modeled exhalation flow may supplement, weight, or replace a faulty flow measured by a failure of an exhalation flow sensor. These systems and methods may assist in identifying an inaccurate flow sensor measurement and/or providing a more accurate flow estimate based on the modeled exhalation flow.

In an aspect, a method for a modeled exhalation flow is provided. The method includes measuring an exhalation pressure of a breathing circuit between a patient and an exhalation valve. The method further includes determining a set valve pressure of the exhalation valve based on at least one parameter associated with the exhalation valve. Additionally, the method includes determining a pressure difference between the determined set valve pressure and the measured exhalation pressure. Based on the determined pressure difference, the method further includes estimating a value for modeled exhalation flow through the breathing circuit.

In an aspect, at least one parameter includes an electrical current provided to the exhalation valve. In another aspect, estimating the value for the exhalation flow is based on a flow estimation model. In yet another aspect, the flow estimation model is a third-degree polynomial. In a further aspect, the flow estimation model is based on the following relationship:

$$Q_{exh,model} = a*\Delta P^3 + b*\Delta P^2 + c*\Delta P + d,$$

where: $Q_{exh,model}$ is the modeled exhalation flow; $\Delta P$ is the determined pressure difference; and a, b, c, and d are coefficients that are determined based on properties of the ventilation system. In yet a further aspect, the determined pressure difference ($\Delta P$) is based on the following relationship:

$$\Delta P = P_{exp} - K_I * I,$$

where: $P_{exp}$ is a measured exhalation pressure; $K_I$ is a conversion constant for the exhalation valve; and I is an electrical current provided to the exhalation valve. In another aspect, the operations further comprise training the flow estimation model.

In another aspect, a ventilator for identifying a sensor failure of an exhalation flow sensor is provided. The ventilator includes a flow sensor; a pressure sensor; an exhalation valve; a processor; and a memory storing computer executable instructions that when executed by the processor cause the ventilator to perform a set of operations. The operations include receiving, from the flow sensor, a measured exhalation flow of breathing gases. The operations further include receiving, from the pressure sensor, a measured pressure. Additionally, the operations include determining a modeled exhalation flow based on at least on parameter of an exhalation valve and the measured pressure. The operations also include evaluating a flow difference between the modeled exhalation flow and the measured exhalation flow. Further, the operations include identifying a sensor failure of the flow sensor based on the flow difference.

In an aspect, the operations further include, in response to determining the sensor failure, use the modeled exhalation flow, instead of the measured exhalation flow, for controlling operation the ventilator. In an aspect, the flow sensor may include a temperature element and a flow element. As an example, the temperature element may be a thermistor. In another example, the flow element may be a hot wire or a hot film. In another aspect, the sensor failure is associated with one or more of: a damaged temperature element and a damaged flow element. As another example, the damaged temperature element may be one or more of: a bent thermistor failure and a contaminated sensor failure. In another example, the damaged flow element may be one or more of: a broken hot wire or hot film failure and saturated filter failure. In yet another aspect, the damaged temperature element is determined based on the flow difference between the modeled exhalation flow and the measured exhalation flow exceeding a threshold. In a further aspect, the broken hot wire or hot film failure is determined based on the measured exhalation flow being a constant value. In another aspect, the saturated filter failure is determined based on a spike in the flow difference. In another aspect, the operations further comprise displaying a failure message indicating the sensor failure. In a further aspect, determining the modeled exhalation flow is based on a difference between the measured pressure and a set valve pressure of the exhalation valve.

In a further aspect, a ventilator for weighting a measured exhalation flow and a modeled exhalation flow is provided. The ventilator includes a flow sensor; a pressure sensor; an exhalation valve; a processor; and a memory storing computer executable instructions that when executed by the processor cause the ventilator to perform a set of operations. The operations include measuring an exhalation flow using the flow sensor. The operations further include measuring an exhalation pressure using the pressure sensor. Additionally, the operations include determining a modeled exhalation flow based on an exhalation valve parameter and the measured exhalation pressure. Further, the operations include evaluating a flow difference between the measured exhalation flow and the modeled exhalation flow. The operations also include generating a weighted average flow based on the measured exhalation flow, the modeled exhalation flow, and the flow difference.

In an aspect, determining the modeled exhalation flow comprises using a flow estimation model trained to determine the modeled exhalation flow. In another aspect, the operation of generating the weighted average flow is based on a determination that the flow difference exceeds a threshold value.

In yet another aspect, a ventilator operating without an exhalation flow sensor is provided. The ventilator includes a pressure sensor; an exhalation valve; a processor; and a memory storing computer executable instructions that when executed by the processor cause the ventilator to perform a set of operations. The operations include receiving, from the pressure sensor, measured exhalation pressure of a breathing circuit between a patient interface and an exhalation valve. The operations further include determining a set valve pressure of an exhalation valve based on at least one parameter associated with the exhalation valve. Additionally, the operations include determining a pressure difference between the set valve pressure and the measured exhalation pressure. The operations also include, based on the pressure difference, estimating a value for modeled exhalation flow through the breathing circuit without using a flow sensor.

In an aspect, the at least one parameter includes an electrical current provided to the exhalation valve. In another aspect, estimating the value for the exhalation flow is based on a flow estimation model. In still another aspect, the flow estimation model is a third-degree polynomial. In yet a further aspect, the flow estimation model is based on the following relationship:

$$Q_{exh,model} = a*\Delta P^3 + b*\Delta P^2 + c*\Delta P + d,$$

where $Q_{exh,model}$ is the modeled exhalation flow; $\Delta P$ is the determined pressure difference; and a, b, c, and d are coefficients that are determined based on properties of the ventilation system. In another aspect, the determined pressure difference ($\Delta P$) is based on the following relationship:

$$\Delta P = P_{exp} - K_I * I,$$

where: $P_{exp}$ is a measured exhalation pressure; $K_I$ is a conversion constant for the exhalation valve; and I is an electrical current being provided to the exhalation valve. In a further aspect, the operations further comprise training the flow estimation model.

It is to be understood that both the foregoing general description and the following Detailed Description are explanatory and are intended to provide further aspects and examples of the disclosure as claimed.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The following drawing figures, which form a part of this application, are illustrative of aspects of systems and methods described below and are not meant to limit the scope of the disclosure in any manner, which scope shall be based on the claims.

Figure 1:
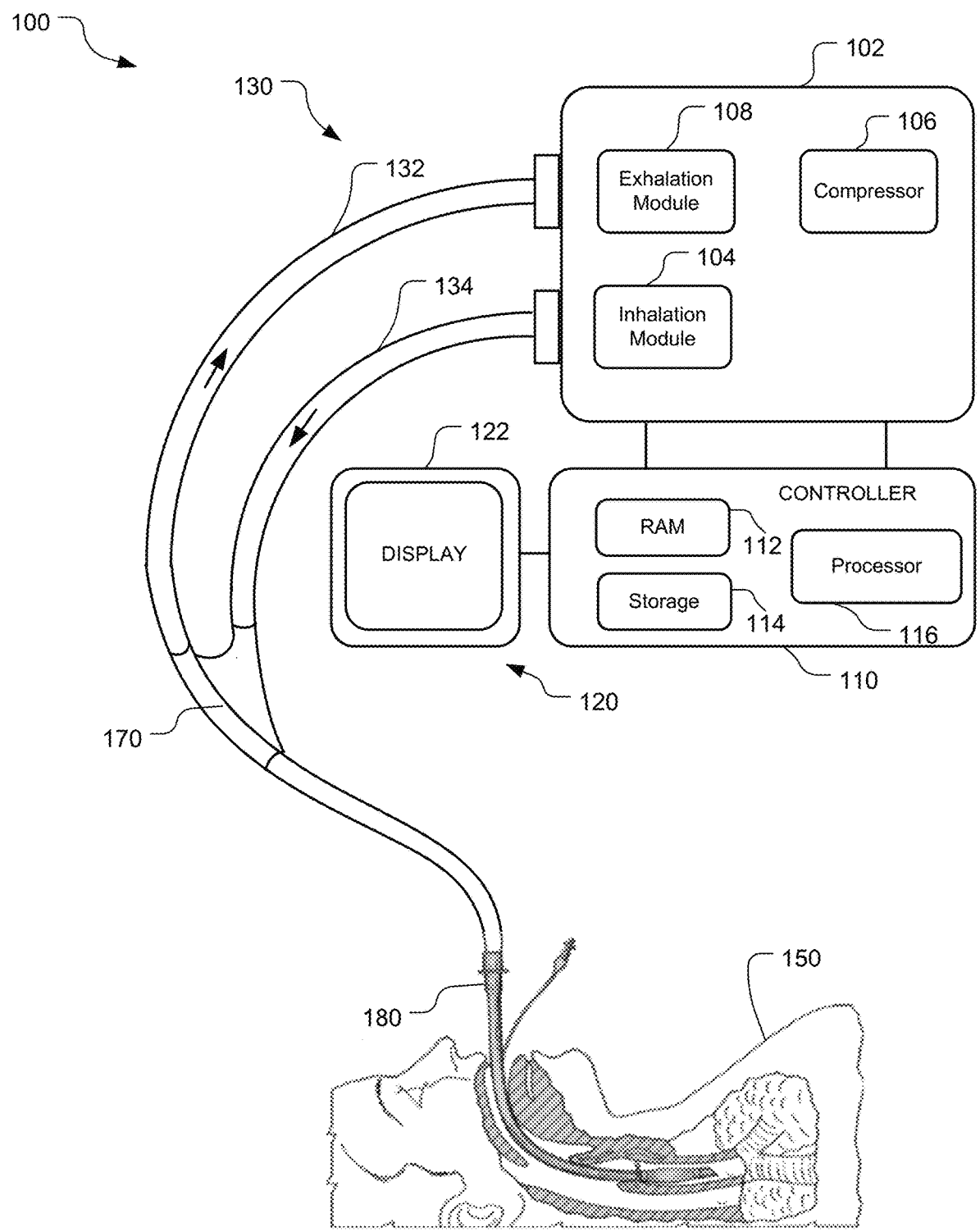
FIG. 1 is a diagram illustrating an example of a ventilator connected to a human patient.

While examples of the disclosure are amenable to various modifications and alternative forms, specific aspects have been shown by way of example in the drawings and are described in detail below. The intention is not to limit the scope of the disclosure to the particular aspects described. On the contrary, the disclosure is intended to cover all modifications, equivalents, and alternatives falling within the scope of the disclosure and the appended claims.

DETAILED DESCRIPTION

As discussed briefly above, medical ventilators are used to provide breathing gases to patients who are otherwise unable to breathe sufficiently. In modern medical facilities, pressurized air and oxygen sources are often available from wall outlets, tanks, or other sources of pressurized gases. Accordingly, ventilators may provide pressure regulating valves (or regulators) connected to centralized sources of pressurized air and pressurized oxygen. The regulating valves function to regulate flow so that respiratory gases having a desired concentration are supplied to the patient at desired pressures and flow rates. Modern ventilators may contain at least one exhalation flow sensor to measure exhalation flow, as well as a pressure sensor near the flow sensor to measure exhalation pressure.

The exhalation flow measured by the flow sensor may be used by the ventilator to adjust parameters and otherwise analyze parameters associated with the patient or the breathing circuit. However, the flow sensor contains components that are easily damaged or impacted and have high rates of failure. For example, the flow sensor components (e.g., thermistor, hot wire/film, etc.) are susceptible to contamination, condensation, debris from nebulization, etc. This may occur during routine interactions with the flow sensor, or even when cleaning the flow sensor. When the flow sensor components are impacted, the exhalation flow determined by the flow sensor may be offset or inaccurate.

As such, systems and methods disclosed herein address these problems by estimating a modeled exhalation flow. The modeled exhalation flow may be used by the ventilator to determine a failure of the flow sensor. Additionally or alternatively, the modeled exhalation flow may be used, in whole or in partial combination with the measured exhalation flow from the flow sensor, to determine a modeled exhalation flow through the exhalation module of the ventilator. With these concepts in mind, several examples of modeled exhalation flow monitoring methods and systems are discussed, below.

FIG. 1 is a diagram illustrating an example of a ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive (e.g., endotracheal tube, as shown) or a non-invasive (e.g., nasal mask) patient interface.

Ventilation tubing system 130 may be a two-limb (shown) or a one-limb circuit for carrying gases to and from the patient 150. In a two-limb example, a fitting, typically referred to as a "wye-fitting" 170, may be provided to couple a patient interface 180 to an inhalation limb 134 and an exhalation limb 132 of the ventilation tubing system 130.

Pneumatic system 102 may have a variety of configurations. In the present example, system 102 includes an exhalation module 108 coupled with the exhalation limb 132 and an inhalation module 104 coupled with the inhalation limb 134. Compressor 106 or other source(s) of pressurized gases (e.g., air, oxygen, and/or helium) is coupled with inhalation module 104 to provide a gas source for ventilatory support via inhalation limb 134. The pneumatic system 102 may include a variety of other components, including mixing modules, valves, sensors, tubing, accumulators, filters, etc.

Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). Controller 110 may include memory 112, one or more processors 116, storage 114, and/or other components of the type found in command and control computing devices. In the depicted example, operator interface 120 includes a display 122 that may be touch-sensitive and/or voice-activated, enabling the display 122 to serve both as an input and output device.

The memory 112 includes non-transitory, computer-readable storage media that stores software that is executed by the processor 116 and which controls the operation of the ventilator 100. In an example, the memory 112 includes one or more solid-state storage devices such as flash memory chips. In an alternative example, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Communication between components of the ventilatory system or between the ventilatory system and other therapeutic equipment and/or remote monitoring systems may be conducted over a distributed network, as described further herein, via wired or wireless means. Further, the present methods may be configured as a presentation layer built over the TCP/IP protocol. TCP/IP stands for "Transmission Control Protocol/Internet Protocol" and provides a basic communication language for many local networks (such as intra- or extranets) and is the primary communication language for the Internet. Specifically, TCP/IP is a bi-layer protocol that allows for the transmission of data over a network. The higher layer, or TCP layer, divides a message into smaller packets, which are reassembled by a receiving TCP layer into the original message. The lower layer, or IP layer, handles addressing and routing of packets so that they are properly received at a destination.

Figure 2:
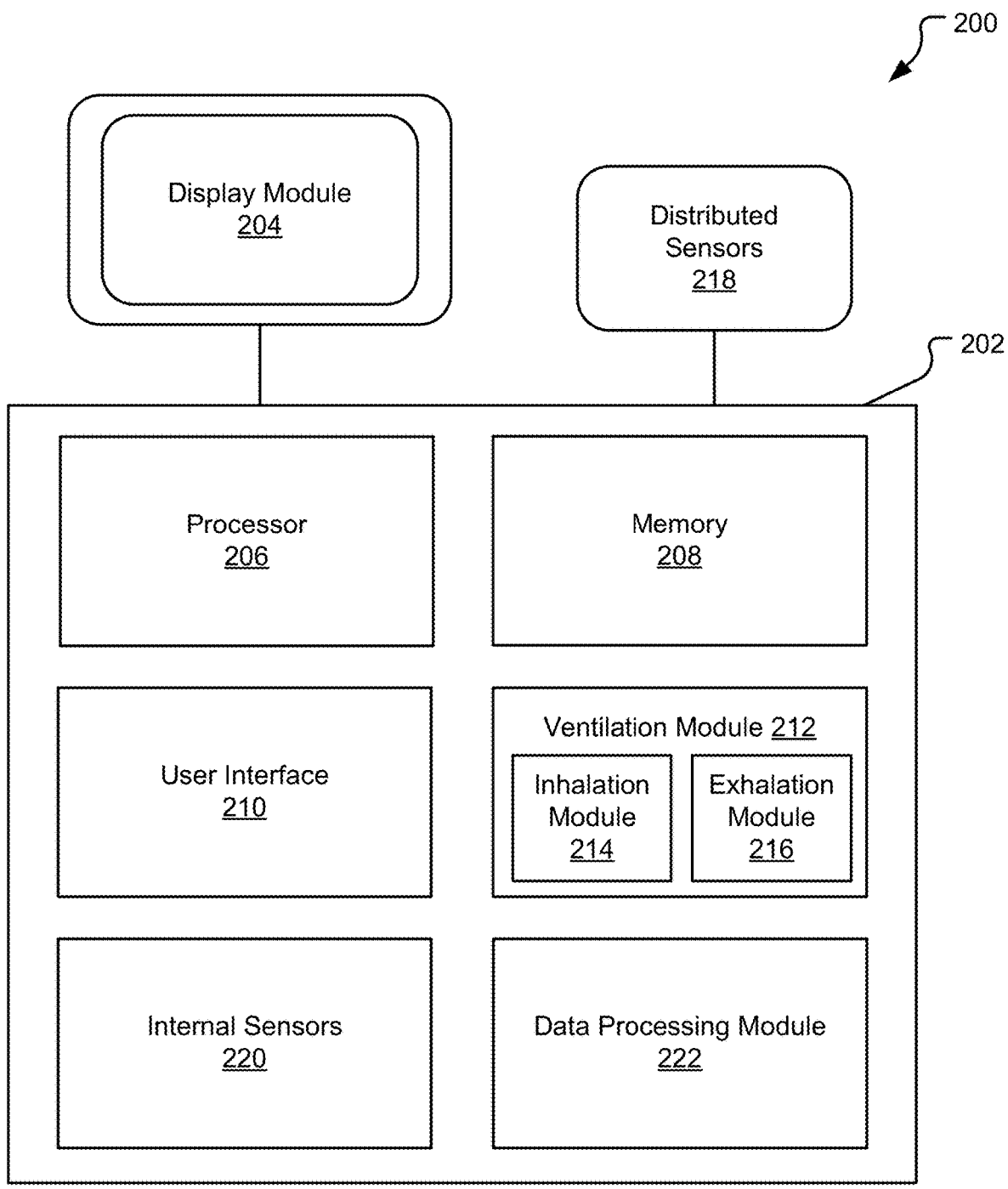
FIG. 2 is a block-diagram illustrating an example of a ventilatory system.

FIG. 2 is a block-diagram illustrating an example of a ventilatory system 200. Ventilatory system 200 includes ventilator 202 with its various modules and components. That is, ventilator 202 may further include, among other things, memory 208, one or more processors 206, user interface 210, and ventilation module 212 (which may further include an inhalation module 214 and an exhalation module 216). Memory 208 is defined as described above for memory 112. Similarly, the one or more processors 206 are defined as described above for one or more processors 116. Processors 206 may further be configured with a clock whereby elapsed time may be monitored by the system 200.

The ventilatory system 200 may also include a display module 204 communicatively coupled to ventilator 202. Display module 204 provides various input screens, for receiving input, and various display screens, for presenting useful information. Inputs may be received from a clinician. The display module 204 is configured to communicate with user interface 210 and may include a graphical user interface (GUI). The GUI may be an interactive display, e.g., a touch-sensitive screen or otherwise, and may provide various windows (i.e., visual areas) comprising elements for receiving user input and interface command operations and for displaying ventilatory information (e.g., ventilatory data, alerts, patient information, parameter settings, etc.). The elements may include controls, graphics, charts, tool bars, input fields, icons, etc. Alternatively, other suitable means of communication with the ventilator 202 may be provided, for instance by a wheel, keyboard, mouse, or other suitable interactive device. Thus, user interface 210 may accept commands and input through display module 204. Display module 204 may also provide useful information in the form of various ventilatory data regarding the physical condition of a patient and/or a prescribed respiratory treatment. The useful information may be derived by the ventilator 202, based on data collected by a data processing module 222, and the useful information may be displayed in the form of graphs, wave representations (e.g., a waveform), pie graphs, numbers, or other suitable forms of graphic display. For example, the data processing module 222 may be operative to determine a modeled exhalation flow and/or flow sensor failure, display information regarding the modeled exhalation flow and/or flow sensor failure, or may otherwise use the modeled exhalation flow and/or flow sensor measured exhalation flow in connection with the ventilator, as detailed herein.

Ventilation module 212 may oversee ventilation of a patient according to ventilatory settings. Ventilatory settings may include any appropriate input for configuring the ventilator to deliver breathable gases to a particular patient, including measurements and settings associated with exhalation flow of the breathing circuit. Ventilatory settings may be entered, e.g., by a clinician based on a prescribed treatment protocol for the particular patient, or automatically generated by the ventilator, e.g., based on attributes (i.e., age, diagnosis, ideal body weight, gender, etc.) of the particular patient according to any appropriate standard protocol or otherwise. In some cases, certain ventilatory settings may be adjusted based on the exhalation flow, e.g., to optimize the prescribed treatment. Ventilatory settings may include inhalation flow, frequency of delivered breaths (e.g., respiratory rate), tidal volume, PEEP, etc.

Ventilation module 212 may further include an inhalation module 214 configured to deliver gases to the patient and an exhalation module 216 configured to receive exhalation gases from the patient, according to ventilatory settings that may be based on the exhalation flow. As described herein, inhalation module 214 may correspond to the inhalation module 104 and 312, or may be otherwise coupled to source(s) of pressurized gases (e.g., air, oxygen, and/or helium), and may deliver gases to the patient. As further described herein, exhalation module 216 may correspond to the exhalation module 108 and 314, or may be otherwise coupled to gases existing the breathing circuit.

Figure 3:
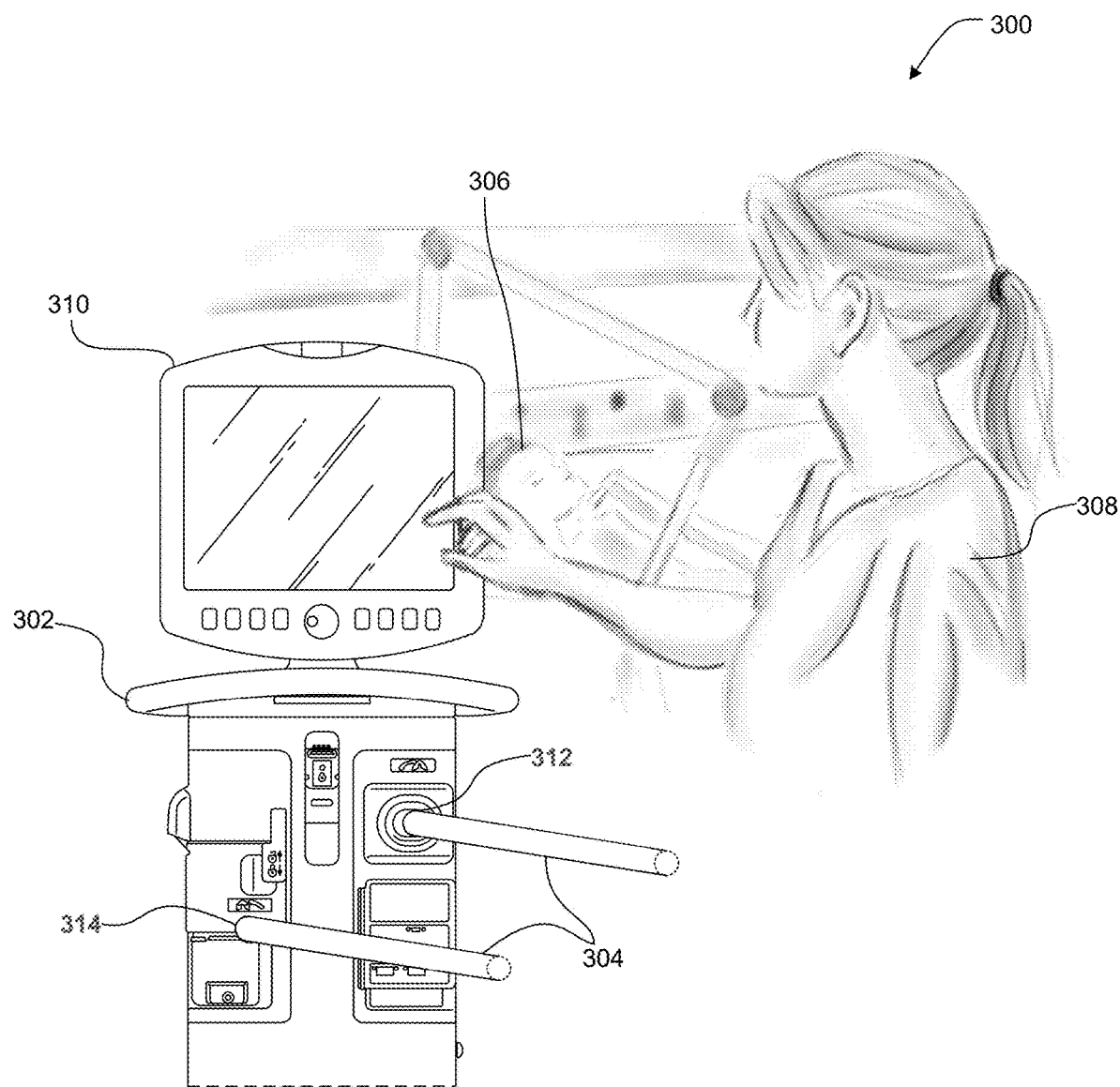
FIG. 3 is an illustration of a schematic diagram that illustrates a ventilator capable of providing interface pressure monitoring during ventilation.

FIG. 3 is an illustration of a schematic diagram 300 that illustrates a ventilator 302 capable of providing interface pressure monitoring during ventilation. As shown, the schematic diagram 300 comprises a ventilator 302, a breathing circuit 304, patient 306, clinician 308, display 310, inhalation module 312, and exhalation module 314. The ventilator 302 may engage one or more data collection sensors (not shown) to monitor various parameters that may be measured or calculated based on the closed system between the ventilator 302 and the patient 306. For example, the data collection sensors may collect one or more of gas flow, pressure, volume, or any other measurement that may be measured, calculated, or derived based on ventilation of the patient 306, measured at both the inhalation module 312 and exhalation module 314 of the ventilator. While measuring and collecting data, the ventilator 302 may analyze, graph, or perform other calculations to determine other desired parameters, such as a modeled exhalation flow at the exhalation module 314. This measured, collected, or calculated data may be used by the clinician 308 or ventilator 302 when determining potential adjustments or changes to settings of the ventilator 302 in order to optimize patient-ventilator interaction.

The ventilator 302 may be capable of determining a modeled exhalation flow of the breathing circuit 304 used to ventilate a patient 306. This modeled exhalation flow may be used or referenced during ventilation to determine if the modeled exhalation flow should be used by the ventilator 302 for other inputs, such as alarms, calculations, etc. Additionally, this modeled exhalation flow may be compared with a measured exhalation flow determined by a flow sensor to determine a status of the flow sensor, such as a saturated filter, a broken hot wire, etc., or to determine how much to weigh the modeled exhalation flow relative to the measured exhalation flow. As another example, the modeled exhalation flow may be combined with the exhalation flow measured by the flow sensor. The modeled exhalation flow may also replace the measured exhalation flow for calculations and control determinations made by the ventilator. For example, based on the modeled exhalation flow, measured exhalation flow, or a combination thereof, the ventilator 302 may cause an alarm to sound, replace the measured exhalation flow with the modeled exhalation flow, determine a weighted exhalation flow based on the measured exhalation flow and the modeled exhalation flow, adjust the delivered flow or other parameters, determine a failure of the flow sensor providing the measured exhalation flow, display the measured exhalation flow and/or the modeled exhalation flow on a display 310, or adjust other parameters, among other actions described herein.

Figure 4A:
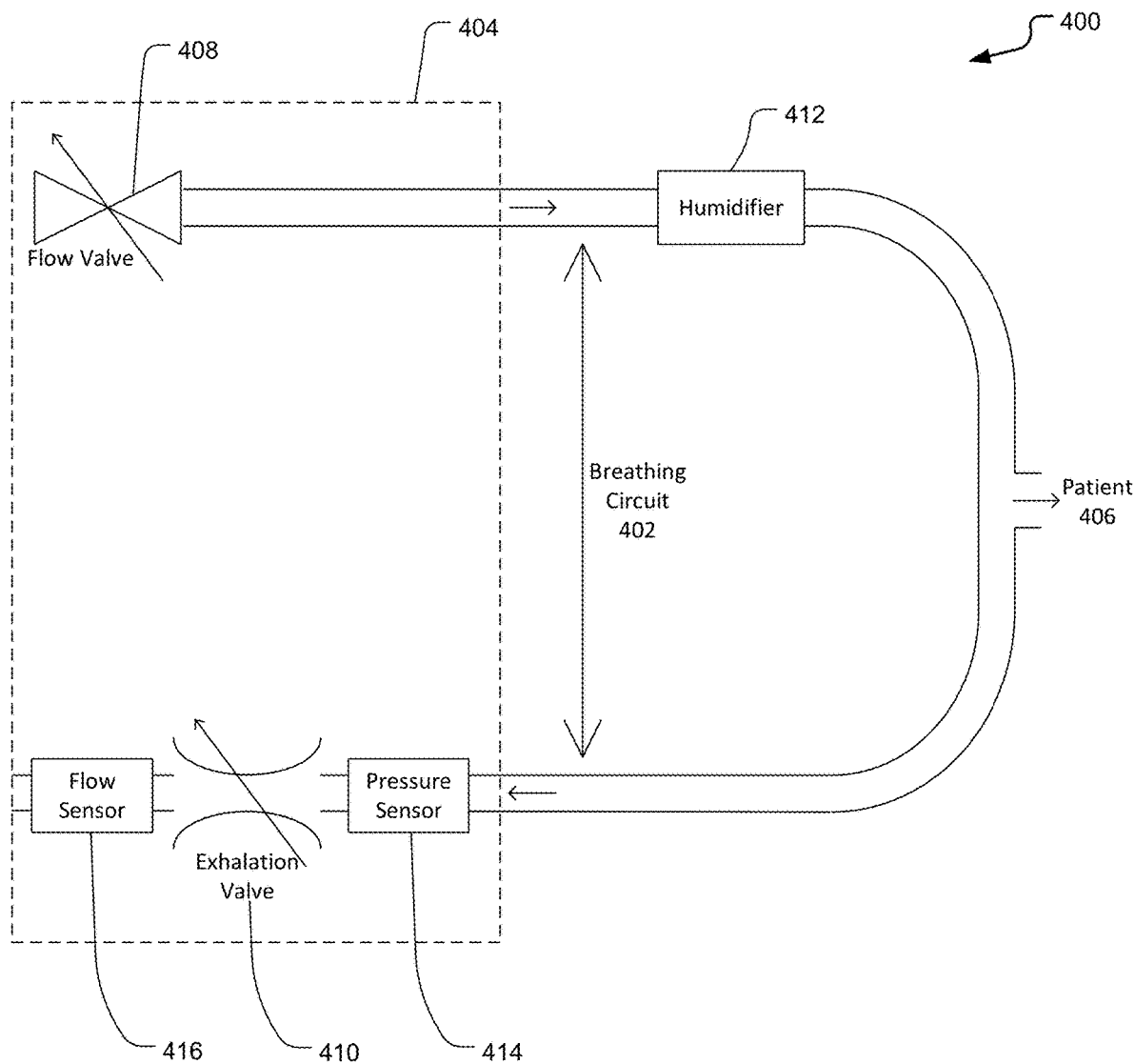
FIG. 4A is an illustration of a schematic diagram of a breathing circuit.

FIG. 4A is a schematic diagram 400 of a breathing circuit 402. As illustrated, the breathing circuit 402 may be coupled to an inhalation module and an exhalation module of a ventilator 404, and may be used to ventilator a patient 406. The ventilator 404 may be capable of adjusting and/or measuring a variety of inhalation and exhalation parameters for the breathing circuit 402. For example, the ventilator 404 may adjust the delivered flow by adjusting a flow valve 408, and may adjust the delivered pressure by adjusting an exhalation valve 410. The exhalation module of the ventilator 404 may also have a pressure sensor 414 and a flow sensor 416, such as the flow sensor. Additionally, a humidifier 412 may be placed along the breathing circuit 402 to humidify the inhalation flow gases to make the patient 406 more comfortable. Although the configuration shown displays components in a particular order, it should be appreciated that components may be in any configuration.

The pressure sensor 414 at the exhalation module of the ventilator 404 may measure a pressure of exhalation gases in the breathing circuit 402 before the exhalation valve 410. The exhalation pressure measured by the pressure sensor 414 may be based in part on a setting of the exhalation valve 410. For example, an open position of the exhalation valve 410 may result in a lower exhalation pressure, while a closed position of the exhalation valve 410 may result in a higher exhalation pressure. It should be appreciated that the exhalation pressure may be additionally based on other variables, including air breathed into the breathing circuit 402 by the patient, the setting of the inhalation flow valve 408, resistance of the breathing circuit, etc. As exhalation pressure measured by the pressure sensor 414 exceeds the settings of the exhalation valve 410, exhalation gases will exit the breathing circuit 402 through the exhalation valve 410 and flow through the flow sensor 416. The flow sensor 416 may have any configuration capable of measuring flow, such as a hot-wire anemometer, a hot plate, cold wire, Vane sensor, etc. Additionally, the flow sensor 416 may have a variety of components to otherwise ensure accuracy of measurements.

Figure 4B:
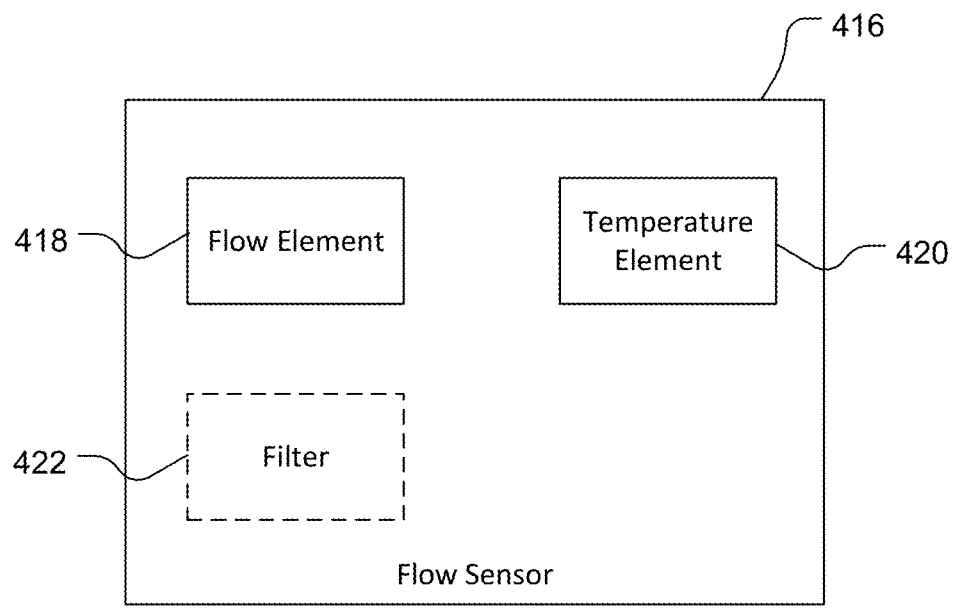
FIG. 4B is an illustration of a schematic diagram of the flow sensor of the breathing circuit show in FIG. 4A.

For example, FIG. 4B illustrates a subcomponent of the schematic diagram 400; the flow sensor 416 of the breathing circuit 402 shown in FIG. 4A. The example flow sensor depicted in FIG. 4B is an anemometer. The flow sensor 416 may have a flow element 418 and a temperature element 420. The flow element 418 and the temperature element 420 may include a variety of components. For example, the flow element 418 of the flow sensor 416 may be a hot film, mesh, and/or wire for use in measuring flow in the anemometer. As another example, a temperature element 420 of the flow sensor 416 may be a thermistor 420. It should be appreciated that other elements may be used other than the hot film and thermistor. An optional filter 422 may be installed upstream of the flow sensor 416 or, alternatively, may be included as a component of the flow sensor 416, as depicted in FIG. 4B. The filter may prevent debris or contaminants from impacting the flow element 418 and/or the temperature element 420. The flow sensor 416 may use measurements or parameters associated with the flow element 418 and/or temperature element 420 to determine a measured exhalation flow through the exhalation valve 410. Those having skill the art will appreciate and understand the operation of a flow sensor or anemometer.

If the flow element 418 is damaged or otherwise impacted (e.g., broken hot wire, broken hot film, saturated filter, contaminated, aged, etc.) and/or if the temperature element 420 is damaged or otherwise impacted (e.g., contaminated, bent thermistor, aged, etc.), then the measured exhalation flow from the flow sensor 416 may be inaccurate. To help alleviate problems that may be caused by such inaccuracies, a modeled exhalation flow may be determined as an estimate of exhalation flow. The modeled exhalation flow may be used, for example, when the flow sensor 416 produces an inaccurate measured exhalation flow. In addition, the modeled exhalation flow may be used in lieu of an exhalation flow sensor, thus saving the costs of including and replacing the flow sensor 416.

The modeled exhalation flow may be determined using a pressure value measured by the pressure sensor 414 at the exhalation module of the ventilator 404 and at least one parameter associated with the exhalation valve 410. For example, a parameter associated with the exhalation valve may be a user setting, an electrical current supplied to the exhalation valve 410, a constant specific to the ventilator 404 or exhalation valve 410, a combination of parameters, etc. The parameter associated with the exhalation valve 410 may be used to determine a set valve pressure of the exhalation valve 410. For example, by knowing the electrical current provided to the exhalation valve 410 along with other valve constants, a set valve pressure of the exhalation valve 410 may be determined. The ventilator may then determine a pressure difference between the measured exhalation pressure (measured by the pressure sensor 414 at the exhalation module of the ventilator 404) and the set valve pressure of the exhalation valve 410 (as determined based on at least the parameter associated with the exhalation valve 410). Based on the pressure difference, the ventilator may estimate a modeled exhalation flow, without otherwise using the flow sensor 416. For example, the modeled exhalation flow may have a polynomial relationship with the pressure difference. As another example, the modeled exhalation flow may be determined based on the equations, below:

$$\Delta P = P_{exh} P_{EV}$$

$$Q_{exh,model} = a * \Delta P^3 + b * \Delta P^2 + c * \Delta P + d,$$

where $\Delta P$ is pressure difference, $P_{exh}$ is the exhalation pressure measured by a pressure sensor, and $P_{EV}$ is the set valve pressure determined based on at least one parameter associated with the exhalation valve, $Q_{exh,model}$ is modeled exhalation flow, a, b, c, and d are constants. The constants may be determined by fitting the polynomial model to a known correct flow measurement. In some examples, the constants are specific to the type of ventilator or components within the ventilator. Accordingly, once the constants have been determined for one ventilator, those constants may be used for other ventilators of the same type. The parameter associated with the exhalation valve may include a user input, an electrical current (I) provided to the exhalation valve, a ventilator-specific conversion constant ($K_I$), etc. As an example, the set valve pressure ($P_{EV}$) may be determined by multiplying the conversion constant ($K_I$) by the electric current (I) provided to the exhalation valve. Such a relationship is represented by the following equation:

$$P_{EV} = I * K_I$$

The conversion constant ($K_I$) may be specific to the valve that is being used. For instance, different valves may have different conversion constants ($K_I$).

The modeled exhalation flow may be used when a failure of the flow sensor 416 occurs. As an example, the flow sensor 416 may fail when one or more of the components of the flow sensor 416 fails. In an example, the flow sensor 416 may fail when the flow element 418 is damaged or impacted and/or when the temperature element 420 is damaged or impacted. In the example where the flow element 418 is a hot wire or hot film, a failure of the flow sensor 416 may be associated with a broken hot wire failure or a broken hot film failure. In another example, the temperature element 420 may be a thermistor. In the example where the temperature element 420 is a thermistor, a failure of the flow sensor 416 may be associated with a bent thermistor failure or contaminated sensor failure. Another failure of the flow sensor 416 may be associated with a saturated filter (e.g., filter 422), which may be upstream of the flow sensor or a component of the flow sensor, as described herein. It should be appreciated that the filter 422 may be an optional component of the ventilator 404, such that a flow sensor 416 may not have an associated filter 422. In an example where the ventilator 404 has a filter 422, a failure of the flow sensor 416 may be associated with a saturated filter 422, which may impact the flow element 418 of the flow sensor 416. Of these example failures, a bent thermistor and broken hot wire may be caused by, at least, insertion of a foreign object (e.g., finger or brush) into the flow sensor 416 or dropping of the flow sensor 416 during handling or cleaning the flow sensor 416. Contaminants may enter the flow sensor 416 when medications are nebulized to the patients. Those medications or other contaminants may coat or stick to the hot wire, hot film, thermistor, or other components of the flow sensor 416, ultimately causing incorrect flow measurements. Additionally, humidification during ventilation may result in a saturated filter. Once the filter 422 becomes saturated, droplets of liquid may permeate through the filter 422 and contact the flow element 418, temperature element 420, or other components of the flow sensor, which may also cause incorrect flow measurements. Examples of these failures are graphically represented in the figures described below in FIGS. 5A-5D.

FIGS. 5A-5D are graphical illustrations 500A, 500B, 500C, 500D of a modeled exhalation flow 510, a measured exhalation flow 508, an inhalation flow measurement 502, an exhalation pressure 504, and an IE phase 506 collected by the ventilator before and after a failure initiation time 512 when a flow sensor failure began. Each of the graphical illustrations shown in FIGS. 5A-5D show examples of different flow sensor failures and how the failure impacts the measured exhalation flow 508 and other measured parameters (e.g., exhalation pressure 504). As may apply to FIGS. 5A-5D, the modeled exhalation flow 510 may be determined based on the methods and systems described herein. The inhalation flow measurement 502, exhalation pressure 504, IE phase 506, and measured exhalation flow 508 may be measured or determined by the ventilator. For example, the inhalation flow measurement 502 may be measured or determined based on at least one parameter associated with a flow valve (e.g., flow valve 408 at the inhalation port) and the exhalation pressure may be measured or determined based on at least one parameter associated with an exhalation valve (e.g., exhalation valve 410 at the exhalation port). The IE phase indicates whether the ventilator is in an inhalation phase or an exhalation phase and is tracked by the ventilator. The measured exhalation flow is the flow measured by the exhalation flow sensor, e.g., the flow sensor, even when damaged.

Figure 5A:
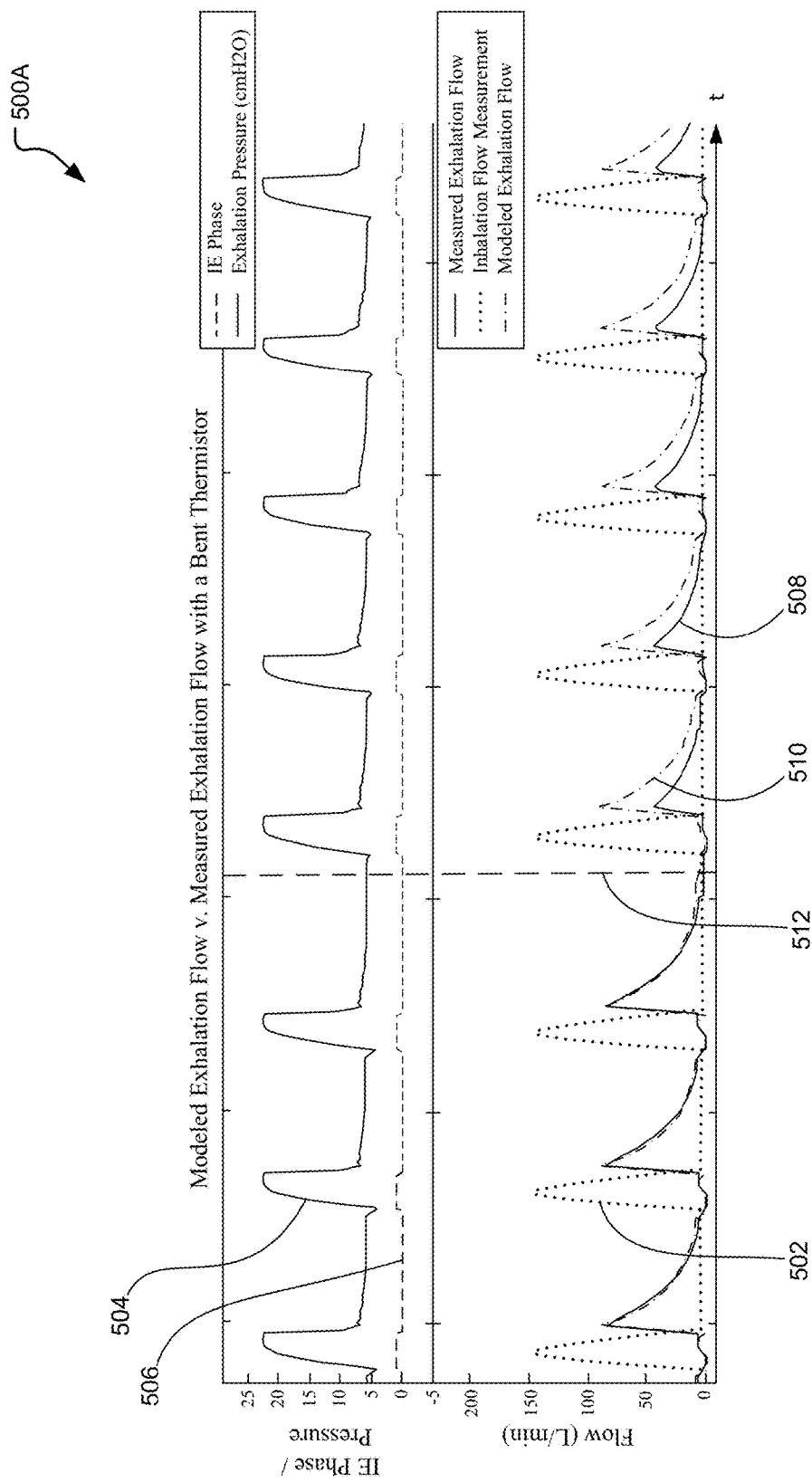
FIGS. 5A-5D are graphical illustrations of a modeled exhalation flow, a measured exhalation flow, and parameters measured and collected by the ventilator before and after a flow sensor failure has occurred.

As an example, FIG. 5A is graphical illustration 500A of a modeled exhalation flow 510, a measured exhalation flow 508, an inhalation flow measurement 502, an exhalation pressure 504, and an IE phase 506 collected, calculated, or determined by the ventilator before and after a failure initiation time 512 when the temperature element of the flow sensor was damaged or impacted. In this example, the temperature element is a thermistor that damaged when the thermistor was bent. As appreciated by one with skill in the art, a temperature element, such as temperature element 420, may be used to estimate a temperature within the flow sensor. Thus, when the temperature element is bent, e.g., when the thermistor is bent, the temperature measurement may be inaccurate or taken at an inaccurate location, ultimately leading to an incorrect flow measurement by the flow sensor. As shown in FIG. 5A, the inhalation flow measurement 502, exhalation pressure 504, IE phase 506, and modeled exhalation flow 508 remain unaffected by the damaged temperature element (e.g., bend in the thermistor) at failure initiation time 512. However, as shown, the measured exhalation flow 510 (from the flow sensor) decreases in amplitude after the damaged temperature element (e.g., bend in the thermistor) at failure initiation time 512. This decrease in amplitude may be substantially uniform, or may result in a variable change in amplitude.

Figure 5B:
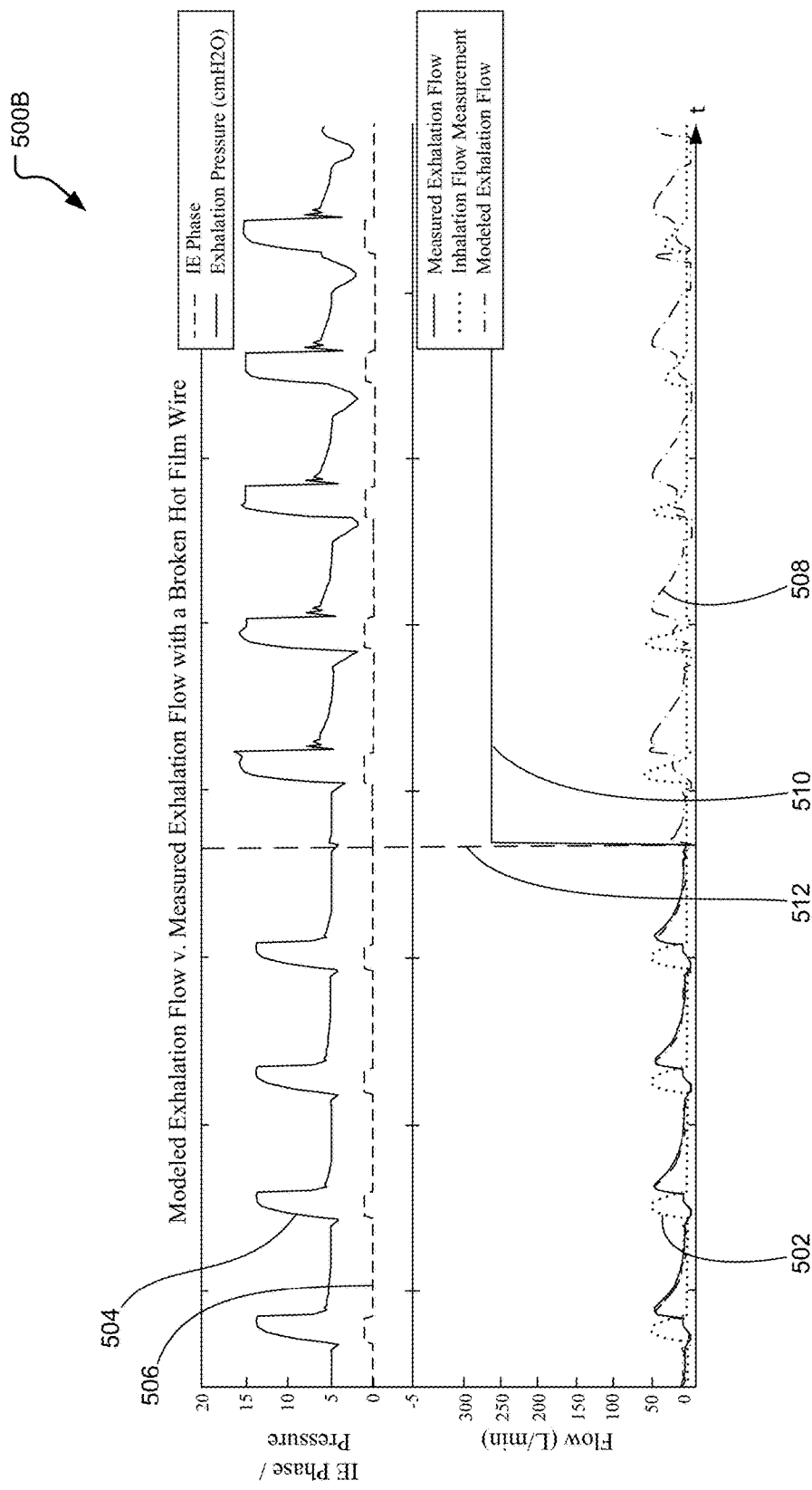

As another an example, FIG. 5B is graphical illustration 500B of a modeled exhalation flow 510, a measured exhalation flow 508, an inhalation flow measurement 502, an exhalation pressure 504, and an IE phase 506 collected, calculated, or determined by the ventilator before and after an failure initiation time 512 when the flow element, such as flow element 418, is damaged. In this example, the flow element is a hot wire that was damaged when the hot wire was broken. This example also applies to a hot film that was damaged when broken.

As appreciated by one with skill in the art, a flow element (e.g., hot wire/film) may be a component of an anemometer, such as the flow sensor, and may be used to estimate a flow rate of gases (e.g., a measured exhalation flow) by determining a resistance, or other electrical property, required to maintain a temperature of hot wire in the anemometer. For example, if the resistance across a hot wire/film increases, then the flow sensor may determine an inaccurate measured exhalation flow. Thus, a break in the hot wire/film may result in a faulty determination or measurement of flow. In this example, the flow sensor may determine a high, constant measured exhalation flow 508 when the flow element is damaged (e.g., the hot wire/film is broken).

As shown in FIG. 5B, the inhalation flow measurement 502, exhalation pressure 504, IE phase 506, and modeled exhalation flow 508 remain substantially unaffected by the damaged flow element (e.g., broken hot wire) at failure initiation time 512. However, as shown, the measured exhalation flow 510 (from the flow sensor) spikes to a high, constant exhalation flow value due to the damaged flow element (e.g., broken hot wire). Thus, in this example, the damaged flow element results a constant, impractically high resistance, which results in the flow sensor providing a flow output corresponding to a high, constant measured exhalation flow 508.

Figure 5C:
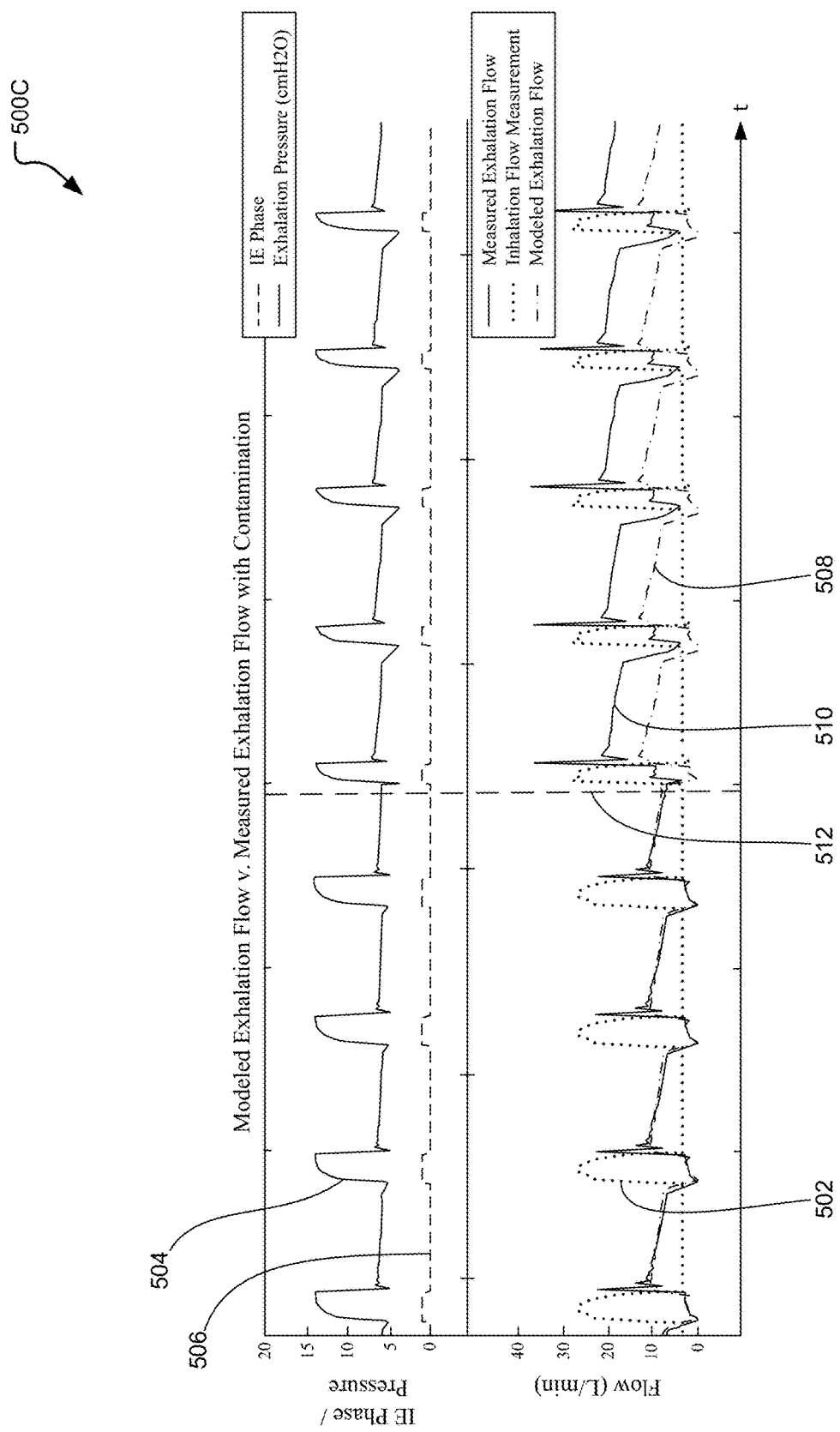

As a further example, FIG. 5C is graphical illustration 500C of a modeled exhalation flow 510, a measured exhalation flow 508, an inhalation flow measurement 502, an exhalation pressure 504, and an IE phase 506 collected, calculated, or determined by the ventilator before and after failure initiation time 512 when the flow sensor is contaminated, impacting the temperature element and/or the flow element of the flow sensor. It should be appreciated that a variety of other circumstances, in addition to contamination, may impact the measurements of the flow element and/or temperature element of the flow sensor and lead to inaccurate measured exhalation flow 508.

As one example, a contaminate that has coated components of the flow sensor, such as the flow element (e.g., hot wire/film) and the temperature element (e.g., thermistor), may change the measured flow rate by the flow sensor. In this example, a contaminated temperature element (e.g., contaminated thermistor) may have an increased or decreased heat transfer, therefore greatly increasing or decreasing the temperature determined by the temperature element which may result in an inaccurate change in the measured exhalation flow 510.

As shown in FIG. 5C, the inhalation flow measurement 502, exhalation pressure 504, IE phase 506, and modeled exhalation flow 508 remain unaffected by the contaminated flow sensor after failure initiation time 512. However, as shown, the measured exhalation flow 510 (from the flow sensor) increases in amplitude after the flow sensor components (e.g., flow element and temperature element) are contaminated at failure initiation time 512, based on increased heat transfer characteristics. Thus, as shown in this example, the contamination of the flow sensor may increase the measured exhalation flow 508.

Figure 5D:
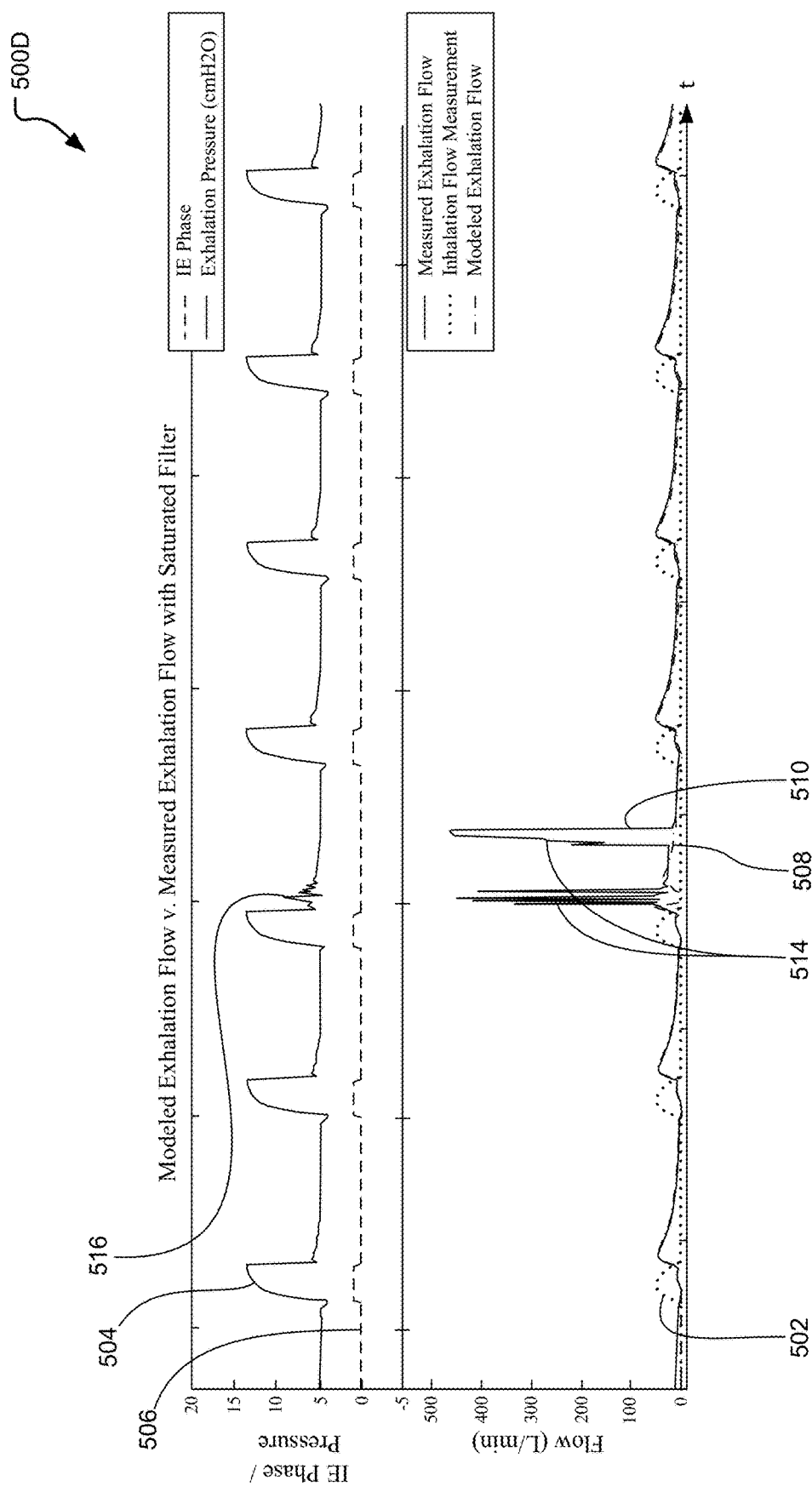

As yet another example, FIG. 5D is graphical illustration 500D of a modeled exhalation flow 510, a measured exhalation flow 508, an inhalation flow measurement 502, an exhalation pressure 504, and an IE phase 506 collected, calculated, or determined by the ventilator before and after large measured flow spikes 514 when the filter is saturated. As appreciated by one with skill in the art, water may be introduced into the breathing circuit (e.g., breathing circuit 402) by a humidifier (e.g., humidifier 412) and exhaled gases breathed into the breathing circuit by the patient (e.g., patient 406). As water accumulates in the breathing circuit, the filter (e.g., filter 422) of the flow sensor (e.g., flow sensor 416) may become saturated. After saturation, droplets of water accumulating on the filter may begin to pass through the filter and contact the flow element and/or temperature element of the flow sensor, which may impact the measured exhalation flow 508 determined by the flow sensor. In an example, water contacting the flow element (e.g. hot wire/film) or temperature element (e.g., thermistor) may rapidly facilitate heat transfer. Due to the increase in heat transfer (i.e., because water has a higher heat transfer coefficient than air), and until the water evaporates or otherwise ceases contact with the components of the flow sensor, the flow sensor may equate the rapid heat transfer with a very high flow rate of gas through the sensor (to otherwise account for the rapid heat transfer).

As shown in FIG. 5D, when the filter is saturated, there is a false pressure spike 516 in exhalation pressure 504. This may result from a change in the exhalation valve command (e.g., current provided to the exhalation valve) reacting to the faulty, measured flow spikes 514. However, the inhalation flow measurement 502 and the IE phase 506 remain unaffected by the filter saturation. The measured exhalation flow 510 (from the flow sensor) is impacted with large measured flow spikes 514.

As may apply to FIGS. 5A-5D, the ventilator may be capable of determining if the measured exhalation flow 508 is inaccurate based on a comparison with the modeled exhalation flow 510. For instance, where the difference between the modeled exhalation flow and the measured exhalation flow exceeds a threshold, a determination may be made that the components of the flow sensor (e.g., flow element, temperature element, etc.) has been damaged or impacted, resulting in a failure of the flow sensor. As a result, the modeled exhalation flow may be used in place of, or in combination with, the measured exhalation flow for control decisions being made by the ventilator.

Additionally, the ventilator may be able to determine a specific failure, or a list of potential failures based on the comparison of the measured exhalation flow 508 and the modeled exhalation flow 510. For instance, if the measured exhalation flow matches any of the patterns described above in FIGS. 5A-5D, the root cause for the failure (e.g., damaged or impacted flow element and/or temperature element) may be predicted. The determined failure may be shown on a display of the ventilator. Specific information about the damaged or impacted flow/temperature element may additionally or alternatively be provided. Additionally or alternatively, the ventilator may replace all, or a weighted portion of, the measured exhalation flow 508 with the modeled exhalation flow 510 to be used by other operations of the ventilator. The ventilator may generate a current (e.g., present or contemporaneous) value for the modeled exhalation flow 510.

Figure 6:
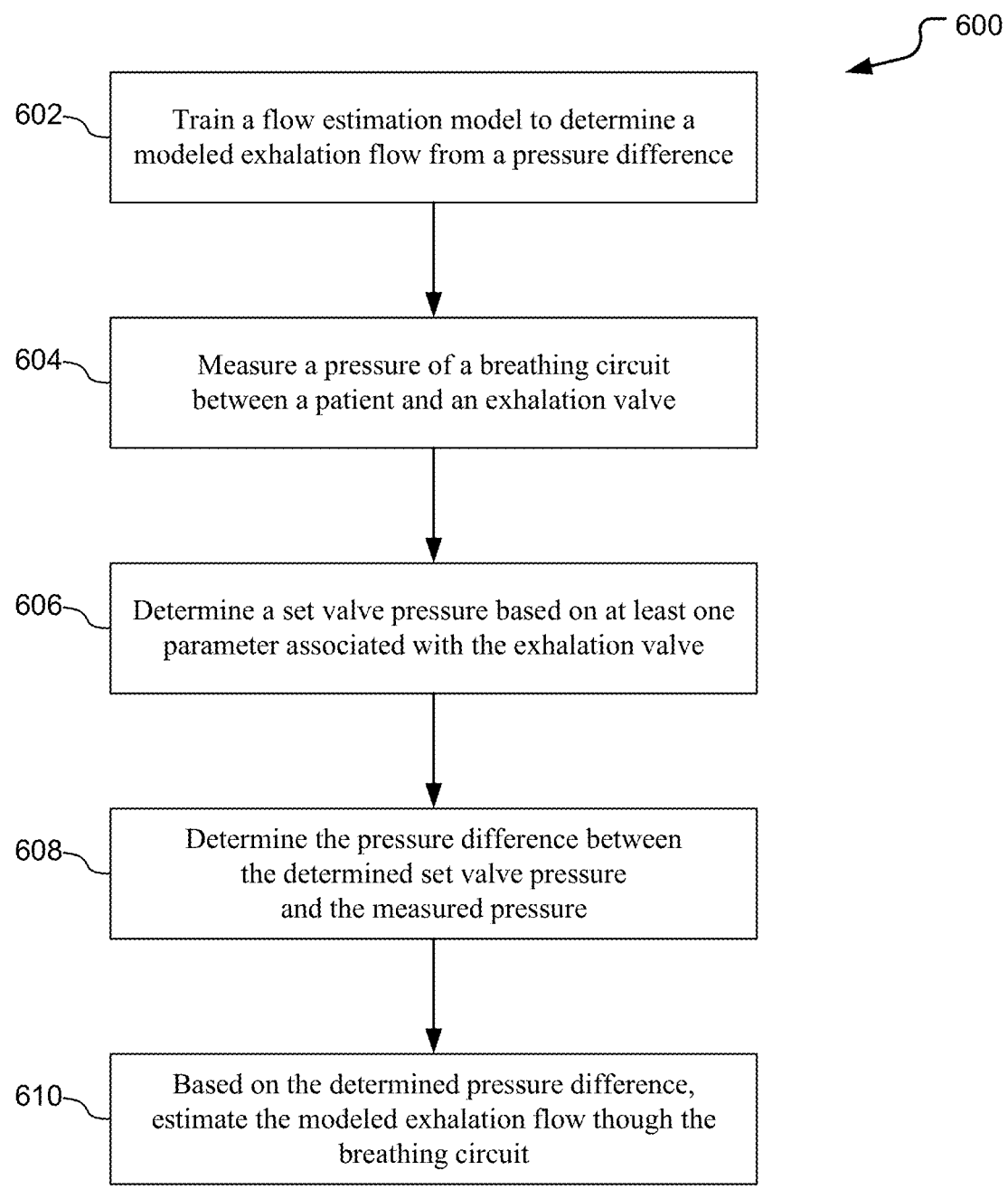
FIG. 6 is a flowchart illustrating a method for estimating a value for modeled exhalation flow through the breathing circuit.
Figure 7:
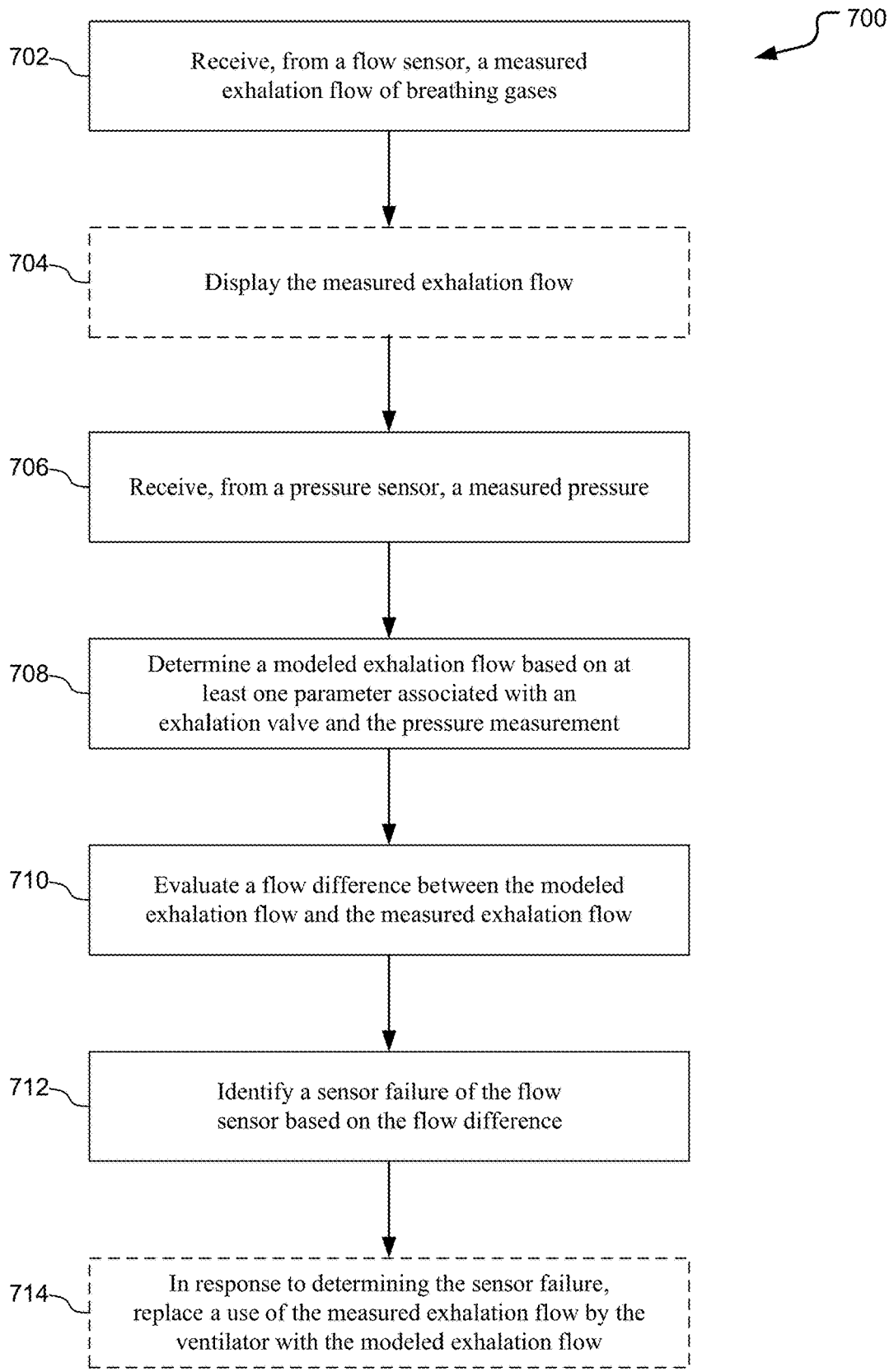
FIG. 7 is a flowchart illustrating a method for identifying a sensor failure of a flow sensor in a breathing circuit.
Figure 8:
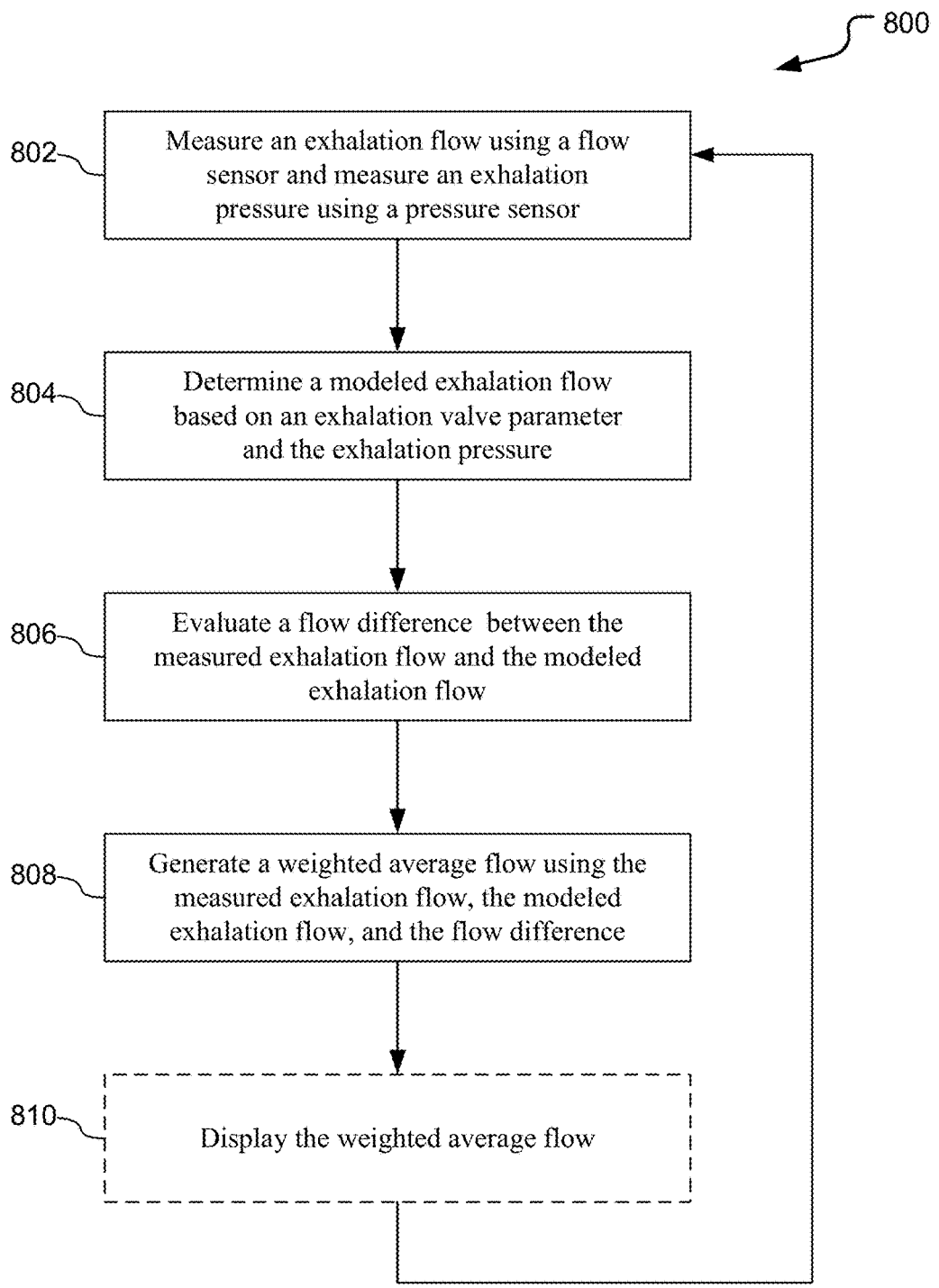
FIG. 8 is a flowchart illustrating a method for generating a weighted average exhalation flow based on a measured exhalation flow, a modeled exhalation flow, and a flow difference.

FIGS. 6-8 illustrate flowcharts of example methods and operations that may be implemented or performed by the systems and devices disclosed herein (e.g., ventilator 100, 202, 302, or 404). Elements of the methods illustrated by dashed borders may represent steps that are optional.

FIG. 6 is a flowchart illustrating a method 600 for estimating a value for modeled exhalation flow through the breathing circuit. Method 600 begins at operation 602 where the ventilator (e.g., ventilator 100, 202, 302, or 404) trains a flow estimation model to determine a modeled exhalation flow from a pressure difference. The flow estimation model may be trained based on patient data collected or stored for one or more patients. Additionally or alternatively, the flow estimation model may be based on empirically derived data and/or characterized empirical properties of the ventilation. For example, the flow estimation model may be based on tube size of the breathing circuit, tube friction, distance between component in the ventilator or along the breathing circuit, type and quantity of components along the breathing circuit, or any other information that may impact flow and/or pressure along any portion of the breathing circuit, including patient parameters. The model may represent a polynomial relationship between modeled exhalation flow and the pressure difference. As another example, the model may be a third-degree polynomial model. As another example, the model may be represented by: $Q_{exh,model} = a*\Delta P^3 + b*\Delta P^2 + c*\Delta P + d$, where $\Delta P = P_{exh} - P_{EV}$, as described above. For example, the constants may be determined by fitting the polynomial model to a set of known correct flow measurements. In some examples, the constants are specific to the type of ventilator or components within the ventilator. Accordingly, once the constants have been determined for one ventilator, those constants may be used for other ventilators of the same type. The model may be updated from time to time.

At operation 604, the ventilator measures a pressure of the breathing circuit between a patient and an exhalation valve. The measured pressure may be determined based on a pressure sensor (e.g., pressure sensor 414). The pressure sensor may be positioned at an exhalation module (e.g., exhalation module 108, 216, 314) of the ventilator, or in fluid communication with an exhalation limb of the breathing circuit.

The method 600 then flows to operation 606 where the ventilator determines a set valve pressure based on at least one parameter associated with the exhalation valve (e.g., exhalation valve 410). For example, the at least one parameter of the exhalation valve may be a user input, a targeted exhalation pressure, a current provided to the exhalation valve, ventilator-specific constants or variables, a voltage applied the exhalation valve, other physical or electrical properties associated with the exhalation valve, etc. The at least one parameter may be one or more parameters, in any combination. Additionally, the ventilator may determine a set valve pressure associated with the at least one parameter of the exhalation valve. The set valve pressure may be used at operation 608, to determine the pressure difference ($\Delta P$) between the determined set valve pressure ($P_{EV}$) and the measured pressure ($P_{exh}$) (e.g., $\Delta P = P_{exh} - P_{EV}$).

At operation 610 where, based on the determined pressure difference, the ventilator estimates the modeled exhalation flow though the breathing circuit. For example, the pressure difference determined in operation 608 may be used in the model trained in operation 602, to determine modeled exhalation flow.

FIG. 7 is a flowchart illustrating a method for identifying a sensor failure of a flow sensor in a breathing circuit. The method begins at operation 702 where the ventilator (e.g., ventilator 100, 202, 302, or 404) may receive, from a flow sensor (e.g., flow sensor 416 or flow sensor), a measured exhalation flow of breathing gases. The measured exhalation flow may be determined by the flow sensor that has a variety of components, including a flow element, temperature element, filter, etc. As described herein, the measured exhalation flow may be influenced by circumstances impacting components of the flow sensor (e.g., flow element, temperature element, etc. damaged or impacted in ways such as a bent thermistor, broken hot wire, contaminated hot wire, saturated filter, etc.). The measured exhalation flow may be provided directly to the ventilator from the flow sensor. Alternatively, the ventilator may determine a measured exhalation flow from raw data or sensor readings of the flow sensor. In an example where the ventilator receives raw data or information about sensor readings of the flow sensor (e.g., temperature reading, provided current, provided voltage, other electrical property, etc. of any or all components of the flow sensor), then the ventilator may have an additional operation of determining the measured exhalation flow from the received raw data or information.

At optional operation 704, the ventilator may display the measured exhalation flow. For example, the measured exhalation flow may be displayed on a display of the ventilator (e.g., display 122, 204, 310). After optional operation 704, the ventilator may continue to operation 706 where the ventilator may receive, from a pressure sensor (e.g., pressure sensor 414), a measured pressure. The pressure sensor may be positioned at an exhalation module (e.g., exhalation module 108, 216, 314) of the ventilator, or in fluid communication with an exhalation limb of the breathing circuit. In examples described herein, the pressure sensor may be located along the breathing circuit between the patient and the exhalation valve.

At operation 708, the ventilator may determine a modeled exhalation flow based on at least one parameter of the exhalation valve (e.g., exhalation valve 410) and the measured pressure (as received from the pressure sensor). The at least one parameter may be any parameter, as described for operation 606 in FIG. 6. The ventilator may determine a set valve pressure associated with the at least one parameter of the exhalation valve. The set valve pressure may be used with the measured pressure to determine a pressure difference. The pressure difference may be used in a model to determine modeled exhalation flow. For example, the model may represent a polynomial relationship between modeled exhalation flow and the pressure difference. As another example, the model may be a third-degree polynomial. As another example, the model may be represented by: $Q_{exh,model} = a*\Delta P^3 + b*\Delta P^2 + c*\Delta P + d$, where $\Delta P = P_{exh} - P_{EV}$, as described above.

After operation 708, the ventilator may evaluate a flow difference between the modeled exhalation flow and the measured exhalation flow, at operation 710. The flow difference may be measured at a specific time, or may be an analysis of flow difference over a period of time, or a combination thereof. For example, the ventilator may determine a flow difference at a specific time and evaluate the flow difference relative to a threshold. As another example, the ventilator may determine a flow difference over a period of time based on measurements or other determinations or analysis by the ventilator. For example, a period of time may span the length of a breath, be based on thresholds of the flow difference or a change in parameters based on the exhalation flow, etc. In an example where the flow difference is evaluated over a period of time, then the ventilator may further evaluate a change in flow difference over the period of time. The flow difference may be associated with an error in the measured exhalation flow. This error, as described herein, may be associated with any number of sensor failures of the flow sensor.

Based on the flow difference, the ventilator may then identify a sensor failure of the flow sensor, at operation 712. As described herein, the flow sensor may fail due to a variety of circumstances, including a damaged or impacted flow element and/or temperature element and, in some instances, specifically a bent thermistor, a broken hot wire, a contaminated hot wire, a saturated filter, or any other failure. The flow difference may be used to determine an associated sensor failure. Additionally, the ventilator may use the flow difference in addition to other measurements or calculations of the ventilator. For example, the ventilator may use the flow difference and the modeled flow and/or measured flow. As an example, specified thresholds of the flow difference may be associated with different sensor failures. Additionally or alternatively, if the flow difference between the modeled exhalation flow and the measured exhalation flow is substantially static or dynamic, then the ventilator may determine that the sensor error may be related to a damaged or impacted temperature element of the flow sensor, such as a bent or contaminated thermistor. As another example, if the flow difference spikes, then the ventilator may determine that the sensor error may be related to a damaged or impacted flow element, e.g., associated with a saturated filter. As yet another example, if the ventilator determines the measured exhalation flow is a constant, then the ventilator may determine that the sensor error may be related to a damaged or impacted flow element, such as a broken hot wire/film. As a further example, if the flow difference continuously increases over time, then the ventilator may determine that the sensor error may be related to an age or lifespan of the flow sensor or any of the components of the flow sensor (such as a flow element and a temperature element), which may be corrected by replacement or recalibration of the flow sensor.

At optional operation 714, the ventilator may, in response to determining the sensor failure, replace a use of the measured exhalation flow by the ventilator with the modeled exhalation flow. Additionally or alternatively, the ventilator may display a failure of the flow sensor. The display of the failure may be specific to the identified failure. Additionally or alternatively, the ventilator may replace the display of the measured exhalation flow with a display of the modeled exhalation flow, or a weighted value based on both the measured exhalation flow and the modeled exhalation flow, which may be based on the flow difference. The measured exhalation flow may be used by the ventilator in a variety of calculation and or adjustments, such as delivered inhalation flow, exhalation valve settings, other exhalation flow parameters, breath triggering, ventilator mode, net flow, lung conditions, other patent, etc.

FIG. 8 is a flowchart illustrating a method for generating a weighted average exhalation flow based on a measured exhalation flow, a modeled exhalation flow, and a flow difference. The method begins are operation 802 where the ventilator (e.g., ventilator 100, 202, 302, or 404) measures an exhalation flow using a flow sensor (e.g., flow sensor 416 or flow sensor), and measures an exhalation pressure using a pressure sensor (e.g., pressure sensor 414).

The method flows to operation 804 where the ventilator determines a modeled exhalation flow based on at least one parameter of the exhalation valve. And operation 806 where the ventilator evaluates a flow difference between the modeled exhalation flow and the measured exhalation flow. Operations 804 and 806 are described herein and may be similar to methods described with respect to operations 708 and 710 of method 700 in FIG. 7.

At operation 808, the ventilator generates a weighted average flow based on the flow difference, the modeled exhalation flow, and the measured exhalation flow. Depending on a magnitude of the flow difference, which may be compared to error thresholds, the ventilator may determine a weighted average flow by weighting the modeled exhalation flow and the measured exhalation flow. In an example where the ventilator has error thresholds, there may be any number of error thresholds. For example, the ventilator may have three error thresholds, such as a small error threshold, a medium error threshold, and a large error threshold. In this example, if the flow difference is below a small error threshold, then the ventilator may give a 100% weight to the measured exhalation flow. If the flow difference exceeds the small error threshold, but remains below the medium error threshold, then the ventilator may assign a 75% weight to the measured exhalation flow and a 25% weight to the modeled exhalation flow. Continuing this example, if the flow difference exceeds the medium error threshold, but remains below the large error threshold, then the ventilator may assign a 50% weight to the measured exhalation flow and a 50% weight to the modeled exhalation flow. As a further example, if the flow difference exceeds the large error threshold, then the ventilator may assign a 100% weight to the modeled exhalation flow. Although these examples use specified number of error thresholds with specified assigned weights, it should be appreciated that the ventilator may have any number of error thresholds with any associated, assigned weights.

Additionally or alternatively, the ventilator may assign weights without reference to error thresholds. For example, the assigned weights may be proportional to the flow difference. As another example, the assigned weights may have specified amounts (e.g., predetermined assigned weights, all-or-nothing 0%/100% assigned weights, etc.). As another example, the assigned weights may be determined from a calculation based on the flow difference, in any mathematical relationship.

At optional operation 810, where the ventilator may display the weighted average flow on a display (e.g., display 122, 204, 310) of the ventilator. Additionally or alternatively, the ventilator may use the weighted average flow in place of the measured exhalation flow in operations of the ventilator.

Although the present disclosure discusses the implementation of these techniques in the context of a ventilator capable of determined a modeled exhalation flow, the techniques introduced above may be implemented for a variety of medical devices or devices utilizing flow sensors. A person of skill in the art will understand that the technology described in the context of a medical ventilator for human patients could be adapted for use with other systems such as ventilators for non-human patients or general gas transport systems. Additionally, a person of ordinary skill in the art will understand that the modeled exhalation flow may be implemented in a variety of breathing circuit setups that may have a flow sensor. Alternatively, the modeled exhalation flow may be implemented without a flow sensor. Further, while described primarily for use with an exhalation flow sensor, the modeled flow techniques described herein may also be performed to model flow at the inhalation port of the ventilator.

Although this disclosure describes determining a modeled exhalation flow based on at least one parameter of the exhalation valve and a measured exhalation pressure, it should be appreciated that other inhalation and exhalation parameters that are adjustable by a ventilator may be used to determine modeled exhalation flow. Additionally, although the methods and systems described herein apply to modeling flow for exhalation gases (e.g., along an exhalation limb or at an exhalation port/module), it should be appreciated that the examples described herein may be applied to a determination of any flow in any portion of the ventilator, based on any valve (e.g., exhalation vale, inhalation valve, etc.). Furthermore, although specific failures of the flow sensor are described and illustrated herein, it should be appreciated that the methods and systems disclosed may be used with a variety of other failures associated with one or more components or elements of the ventilator and/or flow sensor.

Those skilled in the art will recognize that the methods and systems of the present disclosure may be implemented in many manners and as such are not to be limited by the foregoing aspects and examples. In other words, functional elements being performed by a single or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executed or performed substantially concurrently or in reverse order, depending on the functionality and implementation involved.

Further, as used herein and in the claims, the phrase "at least one of element A, element B, or element C" is intended to convey any of: element A, element B, element C, elements A and B, elements A and C, elements B and C, and elements A, B, and C. In addition, one having skill in the art will understand the degree to which terms such as "about" or "substantially" convey in light of the measurements techniques utilized herein. To the extent such terms may not be clearly defined or understood by one having skill in the art, the term "about" shall mean plus or minus ten percent.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A method for operating a ventilator without an operational exhalation flow sensor, comprising:
    measuring an exhalation pressure of a breathing circuit at a pressure sensor associated with an exhalation valve;
    measuring an electrical current provided to the exhalation valve;
    determining a set pressure of the exhalation valve based on the measured electrical current;
    determining a difference between the set pressure and the measured exhalation pressure;
    based on the difference, estimating exhalation flow through the breathing circuit, estimating the exhalation flow is based on a flow estimation model; and
    controlling the exhalation valve based on the estimated exhalation flow.

2. The method of claim 1, wherein the operations further comprise training the flow estimation model.

3. A ventilator, comprising:
    a flow sensor comprising a temperature element or a flow element;
    a pressure sensor;
    an exhalation valve;
    a processor; and
    a memory storing computer executable instructions that when executed by the processor cause the ventilator to perform a set of operations comprising:

receiving, from the flow sensor, a measured exhalation flow of breathing gases;

receiving, from the pressure sensor, a measured pressure;

determining a modeled exhalation flow based on an electrical current provided to an exhalation valve and the measured pressure;

evaluating a flow difference between the modeled exhalation flow and the measured exhalation flow;

identifying a sensor failure of the flow sensor based on the flow difference and; in response to determining the sensor failure, use the modeled exhalation flow, instead of the measured exhalation flow, for controlling operation of the ventilator.

4. The ventilator of claim 3, wherein the sensor failure is associated with one or more of: the temperature element and the flow element.

5. The ventilator of claim 4, wherein the sensor failure associated with the temperature element is one or more of: a bent thermistor failure and a contaminated sensor failure.

6. The ventilator of claim 4, wherein the sensor failure associated with the temperature element is determined based on the flow difference between the modeled exhalation flow and the measured exhalation flow exceeding a threshold.

7. The ventilator of claim 3, wherein the sensor failure is determined to be a broken hot wire failure based on the measured exhalation flow being a constant value.

8. The ventilator of claim 3, wherein the sensor failure is determined to be a saturated filter failure based on a spike in the flow difference.

9. The ventilator of claim 3, wherein the operations further comprise displaying a failure message indicating the sensor failure.

10. The ventilator of claim 3, wherein determining the modeled exhalation flow is based on a difference between the measured pressure and a set valve pressure of the exhalation valve.

11. A ventilator, comprising:
a flow sensor;
a pressure sensor;
an exhalation valve;
a processor; and
a memory storing computer executable instructions that when executed by the processor cause the ventilator to perform a set of operations comprising:
measuring an exhalation flow using the flow sensor;
measuring an exhalation pressure using the pressure sensor;
determining a modeled exhalation flow based on an electrical current provided to the exhalation valve and the measured exhalation pressure;
evaluating a flow difference between the measured exhalation flow and the modeled exhalation flow;
generating a weighted average flow based on the measured exhalation flow, the modeled exhalation flow, and the flow difference; and
using the weighted average flow to control the ventilator to deliver positive pressure ventilation.

12. The ventilator of claim 11, wherein determining the modeled exhalation flow comprises using a flow estimation model trained to determine the modeled exhalation flow.

13. The ventilator of claim 11, wherein the operation of generating the weighted average flow is based on a determination that the flow difference exceeds a threshold value.

* * * * *